US011386715B2

(12) United States Patent
Goto

(10) Patent No.: US 11,386,715 B2
(45) Date of Patent: Jul. 12, 2022

(54) BIOMETRIC APPARATUS, BIOMETRIC SYSTEM, BIOMETRIC METHOD, AND NON-TRANSITORY COMPUTER READABLE RECORDING MEDIUM STORING BIOMETRIC PROGRAM

(71) Applicant: Kazuma Goto, Ishikawa (JP)

(72) Inventor: Kazuma Goto, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 342 days.

(21) Appl. No.: 16/815,149

(22) Filed: Mar. 11, 2020

(65) Prior Publication Data

US 2020/0293801 A1 Sep. 17, 2020

(30) Foreign Application Priority Data

Mar. 14, 2019 (JP) .............................. JP2019-047690

(51) Int. Cl.
*G06V 40/40* (2022.01)
*A61B 5/24* (2021.01)
(Continued)

(52) U.S. Cl.
CPC ................. *G06V 40/45* (2022.01); *A61B 5/24* (2021.01); *A61B 5/242* (2021.01); *A61B 5/2415* (2021.01);
(Continued)

(58) Field of Classification Search
CPC ........ G06V 40/45; A61B 5/24; A61B 5/2415; A61B 5/242; A61B 5/4519; A61B 5/7235;
(Continued)

(56) References Cited

U.S. PATENT DOCUMENTS 8,155,736 B2  4/2012  Sullivan et al.
2005/0131477 A1  6/2005  Meyer et al.
(Continued)

FOREIGN PATENT DOCUMENTS

JP   H10-080409   3/1998
JP   2008-099450  4/2008
(Continued)

OTHER PUBLICATIONS

Yanjuan Geng et al., "Toward attenuating the impact of arm positions on electromyography pattern-recognition based motion classification in transradial amputees", Journal of Neuroengineering and Rehabilitation, Biomed Central, London, GB, vol. 9, No. 1, Oct. 5, 2012, p. 74.

(Continued)

*Primary Examiner* — Brian T Gedeon
(74) *Attorney, Agent, or Firm* — IPUSA, PLLC

(57) ABSTRACT

A biometric apparatus includes a calculation device that processes first time series data from a first measuring device and second time series data from a second measuring device; a display device that displays the time series data; a trigger signal generator that generates one or more trigger signals; and an input unit, wherein the calculation device determines one or more specific intervals of the first time series data based on the one or more trigger signals; configures a classification reference for classifying time series data in the one or more specific intervals using the time series data in a first specific interval using an input signal as a trigger; classifies the second time series data for the one or more specific intervals using a result of classifying the first time series data based on the classification reference; and displays a classification result of the second time series data.

19 Claims, 18 Drawing Sheets

(51) Int. Cl.
*A61B 5/00* (2006.01)
*G06F 16/2458* (2019.01)
*G06K 9/00* (2022.01)
*A61B 5/242* (2021.01)

(52) U.S. Cl.
CPC .......... *A61B 5/4519* (2013.01); *A61B 5/7235* (2013.01); *G06F 16/2477* (2019.01); *G06K 9/0053* (2013.01)

(58) Field of Classification Search
CPC ....... A61B 5/389; A61B 5/7264; A61B 5/407; G06F 16/2477; G06K 9/0053
See application file for complete search history.

(56) References Cited

U.S. PATENT DOCUMENTS

| | | | |
|---|---|---|---|
| 2010/0280334 | A1 | 11/2010 | Carlson et al. |
| 2012/0172743 | A1 | 7/2012 | Aguilar et al. |
| 2018/0369568 | A1 | 12/2018 | Ishibe et al. |
| 2019/0025919 | A1 | 1/2019 | Tadi et al. |
| 2019/0287653 | A1 | 9/2019 | Goto |
| 2021/0102964 | A1* | 4/2021 | Yoshida ........... G01N 35/00623 |

FOREIGN PATENT DOCUMENTS

| | | |
|---|---|---|
| JP | 2008-167975 | 7/2008 |
| JP | 2012-520730 | 9/2012 |
| JP | 5829207 | 12/2015 |
| JP | 2017-099450 | 6/2017 |
| JP | 2019-162253 | 9/2019 |
| WO | 2016028888 | 2/2016 |
| WO | 2018218174 | 11/2018 |

OTHER PUBLICATIONS

The extended European search report for EP20162275.0 dated Aug. 21, 2020.

* cited by examiner

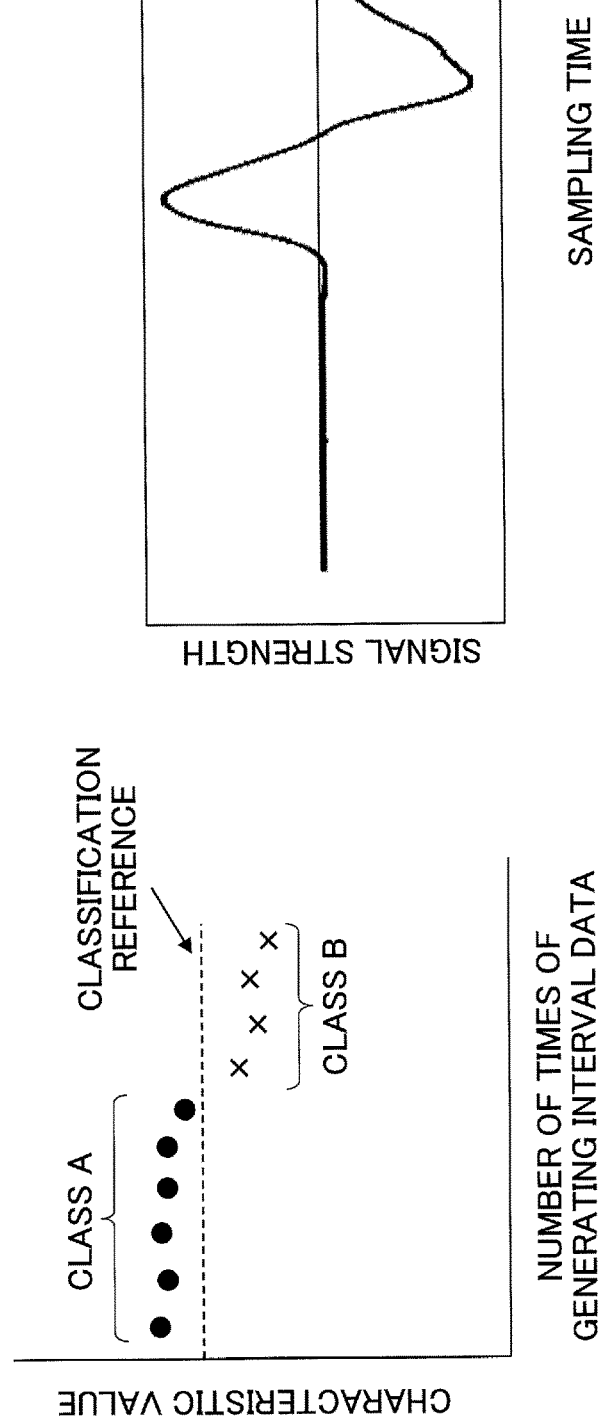

BIOMETRIC APPARATUS, BIOMETRIC SYSTEM, BIOMETRIC METHOD, AND NON-TRANSITORY COMPUTER READABLE RECORDING MEDIUM STORING BIOMETRIC PROGRAM

BACKGROUND OF THE INVENTION

1. Field of the Invention

The present disclosure relates to a biometric apparatus, a biometric system, a biometric method, and a non-transitory computer readable recording medium storing a biometric program.

2. Description of the Related Art

Generally, biological signals are very weak and susceptible to electrical or magnetic noise. Accordingly, when signals including biometric information are received as time-series data, it is not easy to determine whether the signals are from a living organism.

Patent Document 1 (Japanese Unexamined Patent Publication No. H10-80409) discloses a triggering waveform calculation apparatus for determining whether data is suitable for summation by calculating validity of a biological signal by summing and averaging the observed biological signal so as to emphasize the biological signal with respect to a specific stimulus or a response while removing nose, etc.

Patent Document 2 (Japanese Unexamined Patent Publication No. 2017-099450) discloses a nerve stimulating device in which a plurality of stimulating electrodes is arranged on skin and measurement results of nerve activity are fed back to determine a stimulating electrode in which the desired nerve activity is secured to be above a desired level.

Patent Document 3 (PCT Japanese Translation Patent Publication No. 2012-520730) discloses an EEG control system approach for generating a stimulus synchronization average signal for a plurality of EEG (Electroencephalography) signal samples to determine whether the EEG signal samples were induced in response to a stimulus event pattern.

Patent Document 4 (Japanese Unexamined Patent Publication No. 2008-099450) discloses a heart-beat synchronization signal generator included in an ultrasonic diagnostic apparatus in which a mask period and a threshold value, which are configured based on periodicity and a peak value of a first signal, are configured for a second biological signal, and a trigger signal is generated as a heart-beat synchronization signal.

Currently, no method has been proposed for determining whether each of data items for measurement may be used for an arithmetic mean, etc. In addition, no method has been proposed for determining suitability of data for measurement to be used for an arithmetic mean, etc., using data that differs from the data for measurement. Accordingly, it has been required to empirically determine whether data for measurement is suitable to be used for an arithmetic mean, etc., and it has been difficult to determine whether the data is sufficiently accurate to be used for an accurate diagnosis.

There is a need for a biometric apparatus that can obtain biometric information by a simple operation.

SUMMARY OF THE INVENTION

According to an aspect of the present invention, there is provided a biometric apparatus including a calculation device that processes first time series data from a first measuring device that measures biometric information and second time series data from a second measuring device that measures biometric information that differs from the biometric information measured by the first measuring device; a display unit that displays the time series data; a trigger signal generator that generates one or more trigger signals; and an input unit that receives an operation by an operator, wherein the calculation device determines one or more specific intervals of the first time series data based on the one or more trigger signals output from the trigger signal generator, wherein the calculation device configures a classification reference for classifying time series data in the one or more specific intervals using the time series data in a first specific interval of the one or more specific intervals, while using an input signal from the input unit as a trigger, wherein the calculation device classifies the second time series data for the one or more specific intervals using a result of classifying the first time series data based on the configured classification reference, and wherein the calculation device causes the display unit to display a classification result of the second time series data.

With such a configuration, the biometric apparatus can obtain biometric information by a simple operation. Other objects, features and advantages of the present invention will become more apparent from the following detailed description when read in conjunction with the accompanying drawings.

BRIEF DESCRIPTION OF THE DRAWINGS

FIGS. 10A and 10B are diagrams illustrating examples of displaying classification results;

DETAILED DESCRIPTION OF THE PREFERRED EMBODIMENTS

Figure 1:
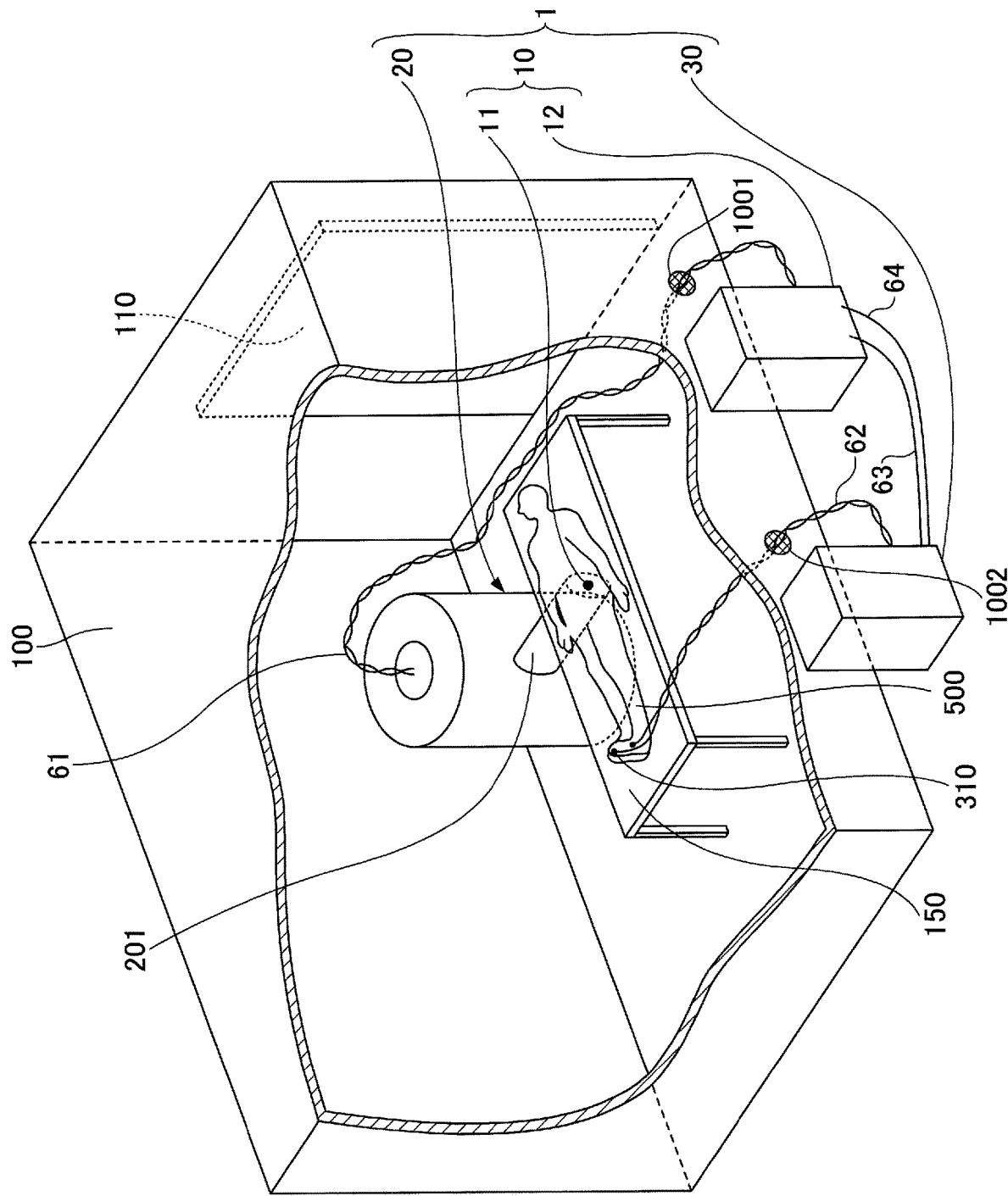
FIG. 1 is a diagram illustrating a spinal cord induced magnetic field measurement system.

In the following, embodiments are described by referring to the drawings. In each drawing, the same components are indicated by the same reference numerals and overlapping descriptions may be omitted. In the following, a sign indicating a signal is also used as a sign indicating a signal value or a signal line. A sign indicating a voltage is also used as a sign indicating a voltage value or a voltage line to which a voltage is supplied.

First Embodiment

This embodiment illustrates an example in which a biometric device is used for a spinal cord induced magnetic field measurement system, which is one of biomagnetic field measurement systems. Namely, in the following, examples are described in which a neural stimulator of the biomagnetic field measurement system is used as a first measuring device and a magnetic measurement device of the biomagnetic field measurement system is used as a second measuring device. Furthermore, a case is described in which a lumbar spine is a part to be measured and a knee joint (fibular head) is a part at which stimulation is input.

FIG. 1 is a diagram illustrating a spinal cord induced magnetic field measurement system.

Referring to FIG. 1, the spinal cord induced magnetic field measuring system 1 includes a magnetic measuring device 10; a cold container 20; and a nerve stimulator 30, as major components. The nerve stimulator 30 is a device that electrically stimulates a nerve from a body surface of a subject 500. The magnetic measuring device 10 includes a SQUID sensor array 11; and a signal processor 12 to measure a magnetic field induced in a living body by electrical stimulation of the nerve stimulator 30. The configuration of the biometric device included in the spinal cord induced magnetic field measurement system 1 is described in FIG. 3.

A portion of the spinal cord induced magnetic field measuring system 1 is located within a magnetic shielding room 100. The magnetic shielding room 100 is used to measure a spinal cord induced magnetic field, which is a weak magnetic field generated by the body. The magnetic shielding room 100 may be formed by laminating, for example, a plate material formed of a permalloy, etc., as a high magnetic permeability material and a plate material formed of an electrically conductive material, such as copper or aluminum.

The magnetic shielding room 100 has an internal space of about 2.5 m×3.0 m×2.5 m, for example, and is provided with a door 110 for transporting devices and for allowing a person to enter or exit the internal space. Similar to the other parts of the magnetic shielding room 100, the door 110 may be formed by laminating a plate material formed of a permalloy, etc., as a high magnetic permeability material and a plate material formed of an electrically conductive material, such as copper or aluminum.

In this specification, a high magnetic permeability material refers to a material having a specific magnetic permeability greater than 1000. Examples of the high magnetic permeability material include, in addition to the permalloy, a single body of iron, nickel, and cobalt, and alloys thereof (including amorphous alloys, powders, and nanoparticles), ferrite, etc.

In the following, the spinal cord induced magnetic field measurement system 1 and its peripheral portions are described in more detail. A table 150 is provided within the magnetic shielding room 100. A cold container 20 is provided within the magnetic shielding room 100, and a signal line 61 used for measurement, control, etc., is connected to the SQUID sensor array 11 in the cold container 20. The signal line 61 is formed of a twisted cable, etc., to reduce magnetic field noise. The signal line 61 is pulled out of the magnetic shielding room 100 through a hole 1001 opened in the magnetic shielding room 100 and is connected to the signal processing unit 12 included in the magnetic measuring device 10.

In the measurement using the spinal cord induced magnetic field measurement system 1, the subject 500 lies supine on a table 150 placed in the magnetic shielding room 100 and the spinal cord induced magnetic field is measured at rest. By performing the measurement at rest, it is possible to reduce, not only the burden on the subject 500, but also the displacement of the measurement device due to unnecessary movement of the subject 500 and magnetic field noise, etc., from muscle caused by muscle tension.

The cold container 20, also referred to as a dewar, retains liquid helium required for a cryogenic operation of the SQUID sensor array 11 for detecting a magnetic field generated from a living body. The cold container 20 includes a protrusion 201 suitable for measuring spinal cord induced magnetic fields, for example, and the SQUID sensor array 11 is located within the protrusion 201. The spinal cord induced magnetic field can be measured with the lumbar spine of the supine subject 500 in contact with the protrusion 201 having the SQUID sensor array 11 installed therein.

Measurement of spinal cord induced magnetic fields requires intentional induction of neuronal activity by electrical stimulation. Electrical stimulation is applied using the nerve stimulator 30. Specifically, the neural stimulator 30 includes an electrode 310, and the electrode 310 is attached to a part of the body of the subject 500. The electrical stimulation is applied to the subject through the electrode 310. The electrode 310 includes at least a stimulation anode and a stimulation cathode and is attached to skin at which electrical stimulation can be efficiently applied to a peroneal nerve, etc., in the knee joint of the subject 500.

The electrode 310 has a signal line 62 attached thereto to provide a stimulus. The signal line 62 may be formed of twisted cables, etc., to reduce magnetic field noise. The signal lines 62 are drawn out of the magnetic shielding room 100 through a hole 1002 which is opened in the magnetic shielding room 100. The signal lines 62 are connected to a main body (other than the part of the electrode 310) of the neural stimulator 30 located outside the magnetic shielding room 100. The neural stimulator 30 is connected to the signal processing unit 12 by the signal lines 63 and 64.

To induce neural activity in subject 500, the nerve stimulator 30 can cause a pulsed electric current to flow between the stimulating anode and stimulating cathode of electrode 310. For example, a pulsed electric current of several mA is applied at several Hz, as the electrical stimulation during spinal cord induced magnetic field measurement. The SQUID sensor array 11 detects the induced magnetic field from the spinal cord due to the neural activity induced by this electrical stimulation.

Figure 2:
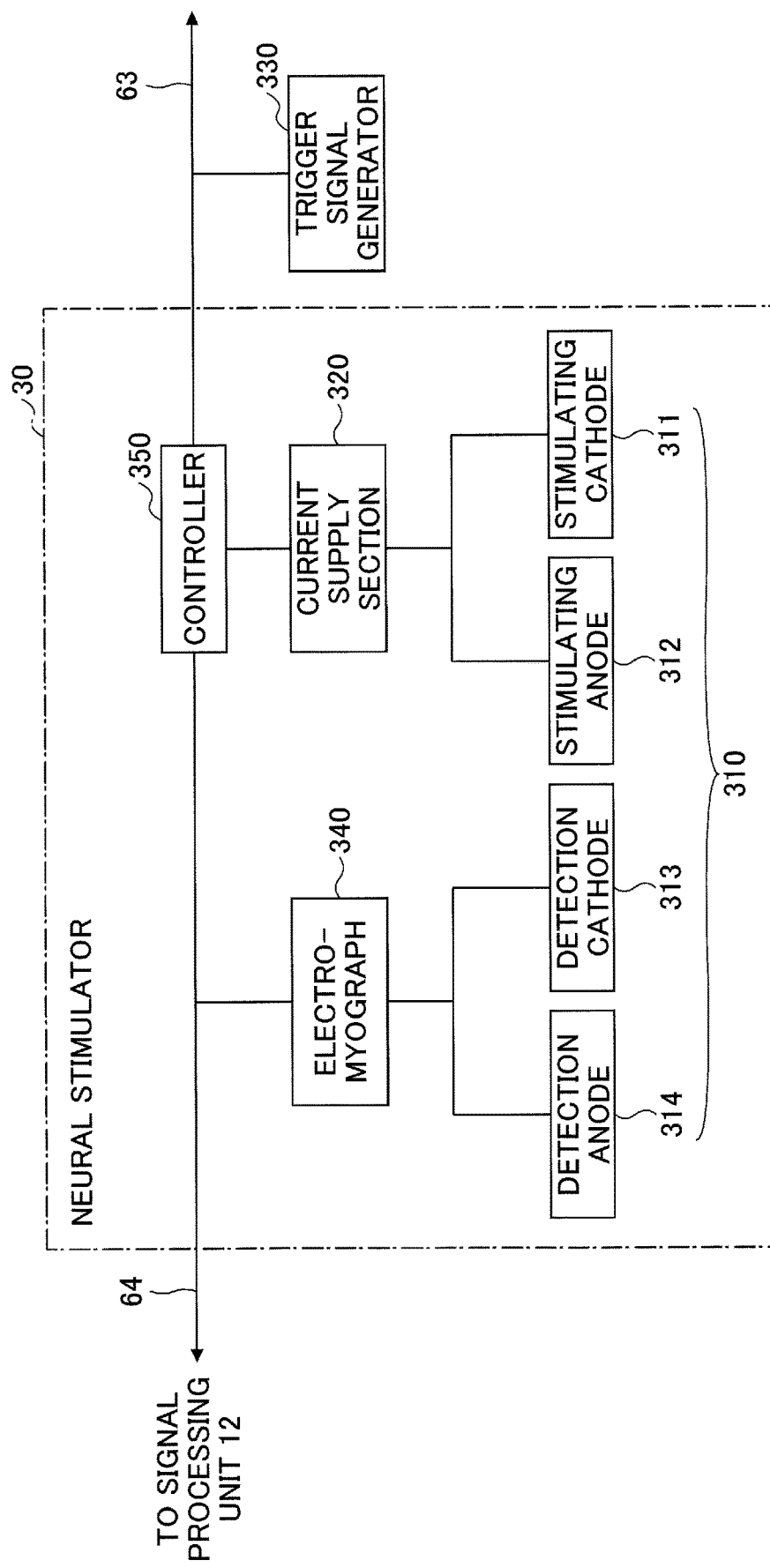
FIG. 2 is a diagram illustrating a neural stimulator in FIG. 1.

FIG. 2 is a diagram illustrating the neural stimulator 30 of FIG. 1. As illustrated in FIG. 2, the neural stimulator 30 includes an electrode 310 (i.e., the stimulating cathode 311, the stimulating anode 312, the detection cathode 313, and the detection anode 314), a current supply section 320, a trigger signal generator 330, an electromyograph 340, and a controller 350. The current supply section 320 is an example of a stimulation section that provides electrical stimulation to the living body to be measured.

The electrode 310 is an electrode arranged on the skin and has the stimulating cathode 311, the stimulating anode 312, the detection cathode 313, and the detection anode 314. The stimulating cathode 311 is the cathode side of the stimulating electrode for inducing nerve activity upon electrical stimulation. The stimulating anode 312 is the anode side of the stimulating electrode for inducing neural activity upon electrical stimulation. The detection cathode 313 is the cathode side of the detection electrode for measuring the action potential (electromyogram) of muscle by electromyograph 340. The detection anode 314 is the anode side of the detection electrode for measuring the action potential of muscle by electromyograph 340.

The current supply section 320 is a circuit for supplying the stimulating current, etc., to the stimulating cathode 311.

The trigger signal generator 330 is a mechanism for generating a trigger signal in accordance with a current supply timing at the current supply 320. The trigger signal generated by the trigger signal generator 330 is transmitted to the signal processing unit 12 (FIG. 1) through the signal line 63 and processed by the signal processing unit 12 and the calculation device 40.

The electromyograph 340 is a device that measures the action potential between the detection cathode 313 and the detection anode 314. The electromyograph 340 transmits a measurement signal to the controller 350 and transmits a measurement signal to the signal processing unit 12 via the signal line 64. The measurement signal obtained from the electromyograph 340 is processed by the signal processing unit 12 and the calculation device 40.

The controller 350 is an information processing device that transmits and receives commands and data between the current supply section 320 and the electromyograph 340. For example, the controller 350 controls operation of the current supply section 320, the electromyograph 340, and the trigger signal generator 330. The controller 350 may be configured to include, for example, a CPU (Central Processing Unit), ROM (Read Only Memory), RAM (Random Access Memory), main memory, etc.

In this case, various functions of the controller 350 can be implemented by a program stored in a ROM, etc., being read out to a main memory and executed by the CPU. The CPU of the controller 350 can read and store data from the RAM, if necessary. However, some or all of the controller 350 may be implemented only in hardware. The controller 350 may also be configured physically by a plurality of devices, etc. The controller 350 may also include a hard disk device, an optical disk device, etc.

Figure 3:
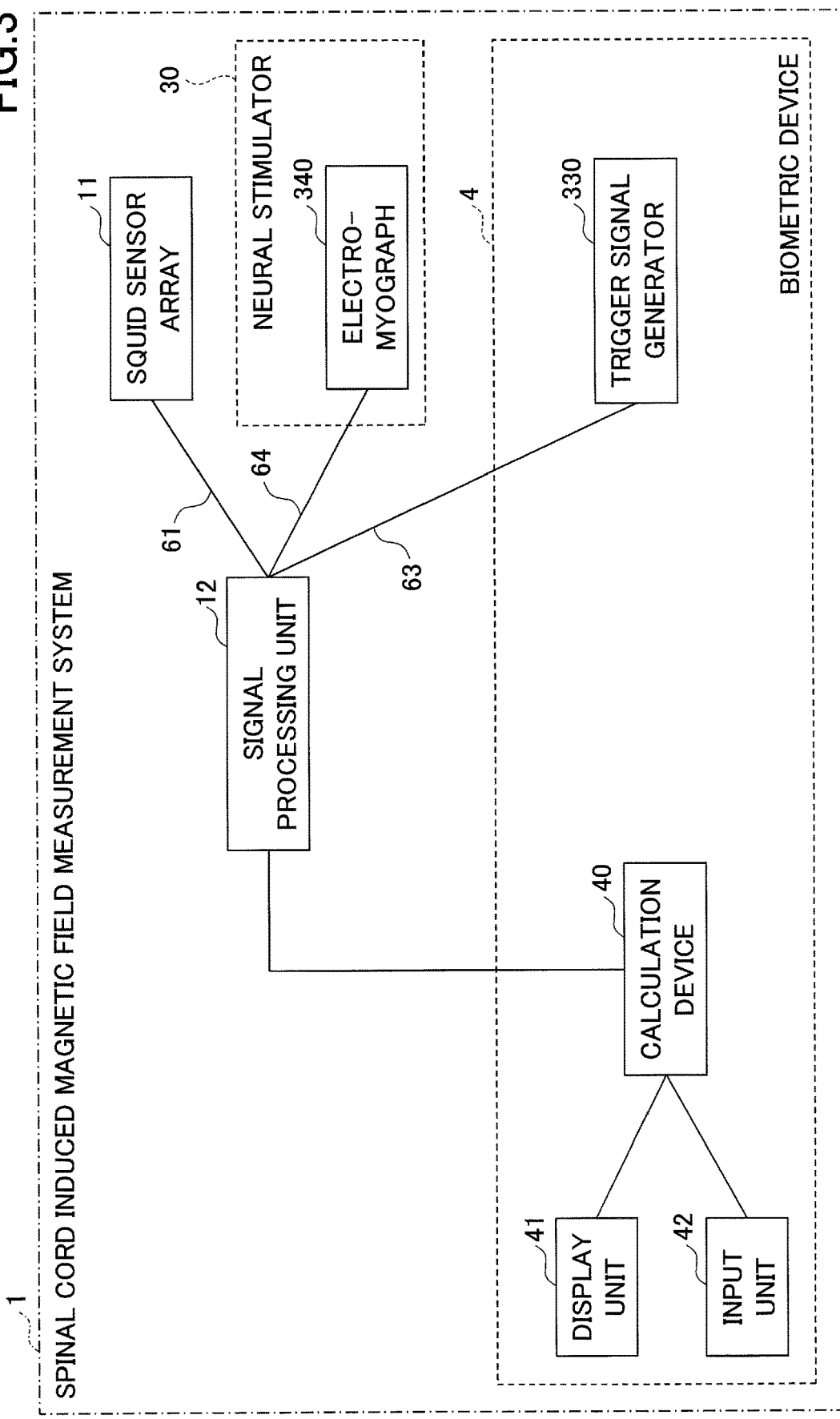
FIG. 3 is a diagram illustrating an example of a biometric device using a spinal cord induced magnetic field measurement system according to a first embodiment.

FIG. 3 is a diagram illustrating an example of the biometric device 4 using the spinal cord induced magnetic field measurement system 1 according to the first embodiment. In FIG. 3, only the components relating to the embodiments are described, and other components, such as the cold container 20, are omitted.

The biometric device 4 includes a calculation device 40; a display unit 41; an input unit 42; and a trigger signal generator 330. The calculation device 40 processes the biological information received from the signal processing unit 12, presents the information regarding the processed biometric information to the display unit 41, and performs processing based on the input signal from the input unit 42. The signal processing unit 12 transmits signals obtained from the SQUID sensor array 11, the electromyograph 340, and the trigger signal generator 330 to the calculation device 40 as time series data. The calculation device 40 processes biometric information by the process described below.

The display unit 41 displays data processed by the calculation device 40. The display 41 includes a device that includes a display, a speaker, and any other means of notification. In this embodiment, a display is used as an example of the display unit 41.

The input unit 42 is responsive to an input by an operator operating the spinal cord induced magnetic field measurement system 1 and transmits a signal corresponding to the input to the calculation device 40. The input unit 42 includes a mouse, a keyboard, and any input device. In the present embodiment, a mouse is used as an example of the input unit 42.

For example, the calculation device 40 is a computer device including a CPU for executing a program. For example, the calculation device 40 executes a biometric program for executing a process illustrated in the flow diagram of FIG. 4, which is described below.

The display unit 41 and the input unit 42 are connected to the calculation device 40. Although not illustrated in FIG. 3, the calculation device 40, the display unit 41, and the input unit 42 are disposed in a room in which the magnetic shielding room 100 is installed, a room which is adjacent to the room in which the magnetic shielding room 100 is installed, etc.

Next, the details of the processing in the calculation device 40 are described. In the description of the details of the processing in the calculation device 40, the electromyograph 340 is referred to as a first measuring device, and the SQUID sensor array 11 is referred to as a second measuring device.

Figure 4:
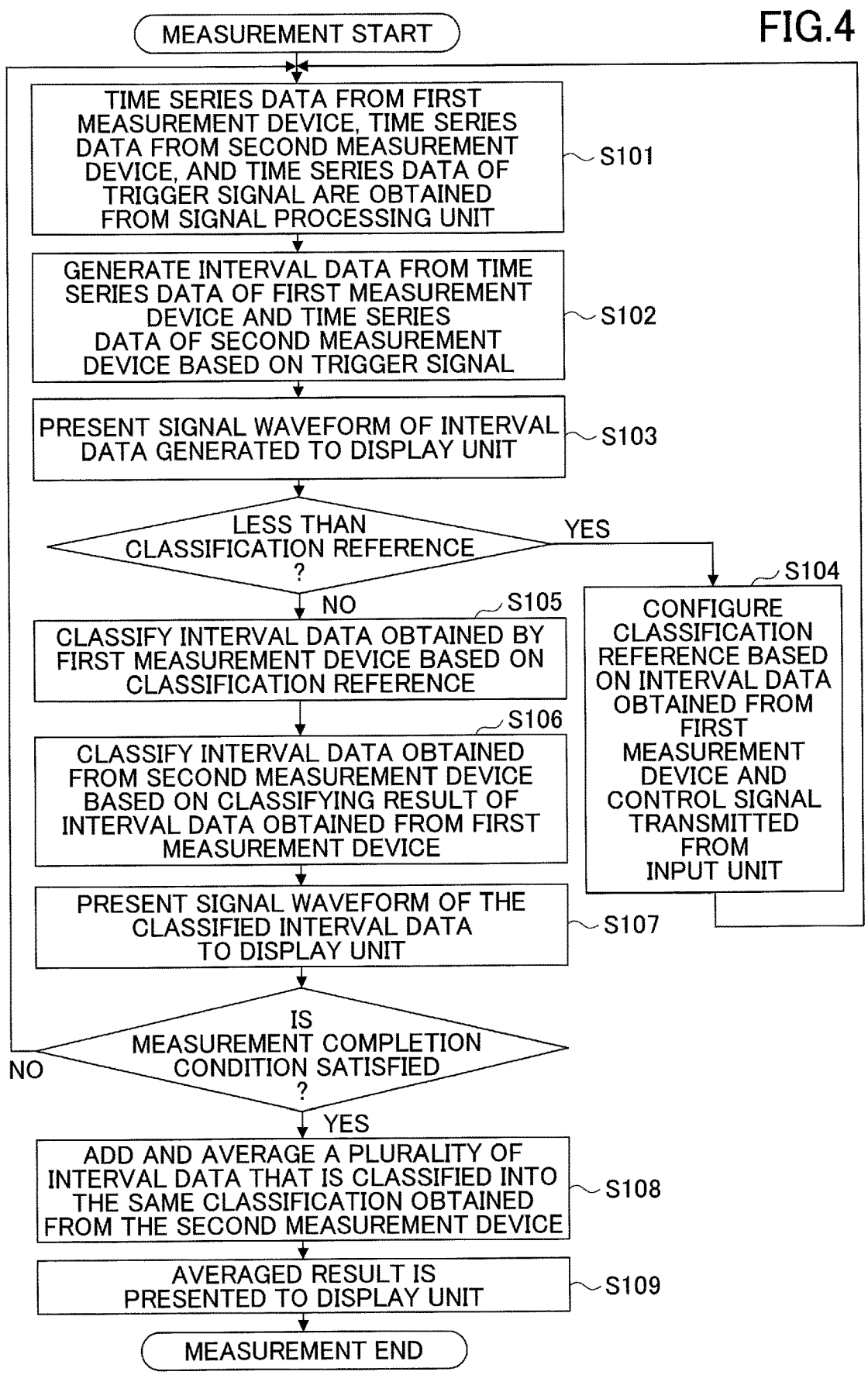
FIG. 4 is a flow diagram of a whole procedure in the calculation device in FIG. 3.

FIG. 4 is a flow diagram of the entire process in the calculation device 40 of FIG. 3. Namely, FIG. 4 illustrates an example of a biometric method performed by the calculation device 40 and a biometric program performed by the calculation device 40.

In the example illustrated in FIG. 4, the processing of steps S101, S102, S103, and S104 is repeated from after the start of the measurement until a classification reference is configured. When the classification reference is configured, the process of steps S101, S102, S103, S105, S106, and S107 is repeated until the measurement completion condition is satisfied. When the measurement completion condition is satisfied, the process of steps S108 and S109 is performed to terminate the measurement.

First, in step S101, the calculation device 40 obtains the time series data from the first measuring device 340, the time series data from the second measuring device 11, and the time series data of the trigger signal from the trigger signal generator 330 through the signal processing unit 12. Next, in step S102, the calculation device 40 generates the interval data from the time series data of the first measuring device 340 and the time series data of the second measuring device 11 based on the trigger signal. Next, in step S103, the calculation device 40 presents the signal waveform of the interval data generated in step S102 to the display unit 41.

When the classification reference is not configured, in step S104, the calculation device 40 configures the classification reference based on the interval data obtained from the time-series data (waveform data) of the first measuring device 340 and the control signal (input signal) transmitted from the input unit 42 (FIG. 3). That is, the calculation device 40 configures a classification reference for classifying the time series data of the specific interval by using the time series data of the specific interval upon receiving the input signal from the input section 42 as a trigger. Thereafter, the process returns to step S101.

When the classification reference is configured, in step S105, the calculation device 40 classifies the interval data (waveform data) obtained by the first measuring device 340 based on the classification reference configured in step S104. A method of classification is described in FIG. 7.

Next, in step S106, the calculation device 40 classifies the interval data obtained from the second measuring device 11 based on the classification result in step S105. Next, in step S107, the calculation device 40 presents the signal waveform of the interval data classified in step S106 to the display unit 41.

Next, when the measurement termination condition is not satisfied, the calculation device 40 returns the processing to step S101. For example, the measurement termination condition is to obtain a predetermined number of time series data items (e.g., 2000 items). When the measurement completion condition is satisfied, in step S108, the calculation device 40 adds and averages a plurality of interval data items that is classified into the same classification among the interval data items obtained from the second measuring device 11. That is, the calculation device 40 calculates an arithmetic mean of the time series data of a plurality of specific intervals classified into the same type. Next, in step S109, the calculation device 40 presents the signal waveform, which is the arithmetic mean result in step S108, to the display unit 41 and ends the measurement processing. Note that the interval data items to be added and averaged are classified as the interval data items satisfying the classification reference.

Figure 5:
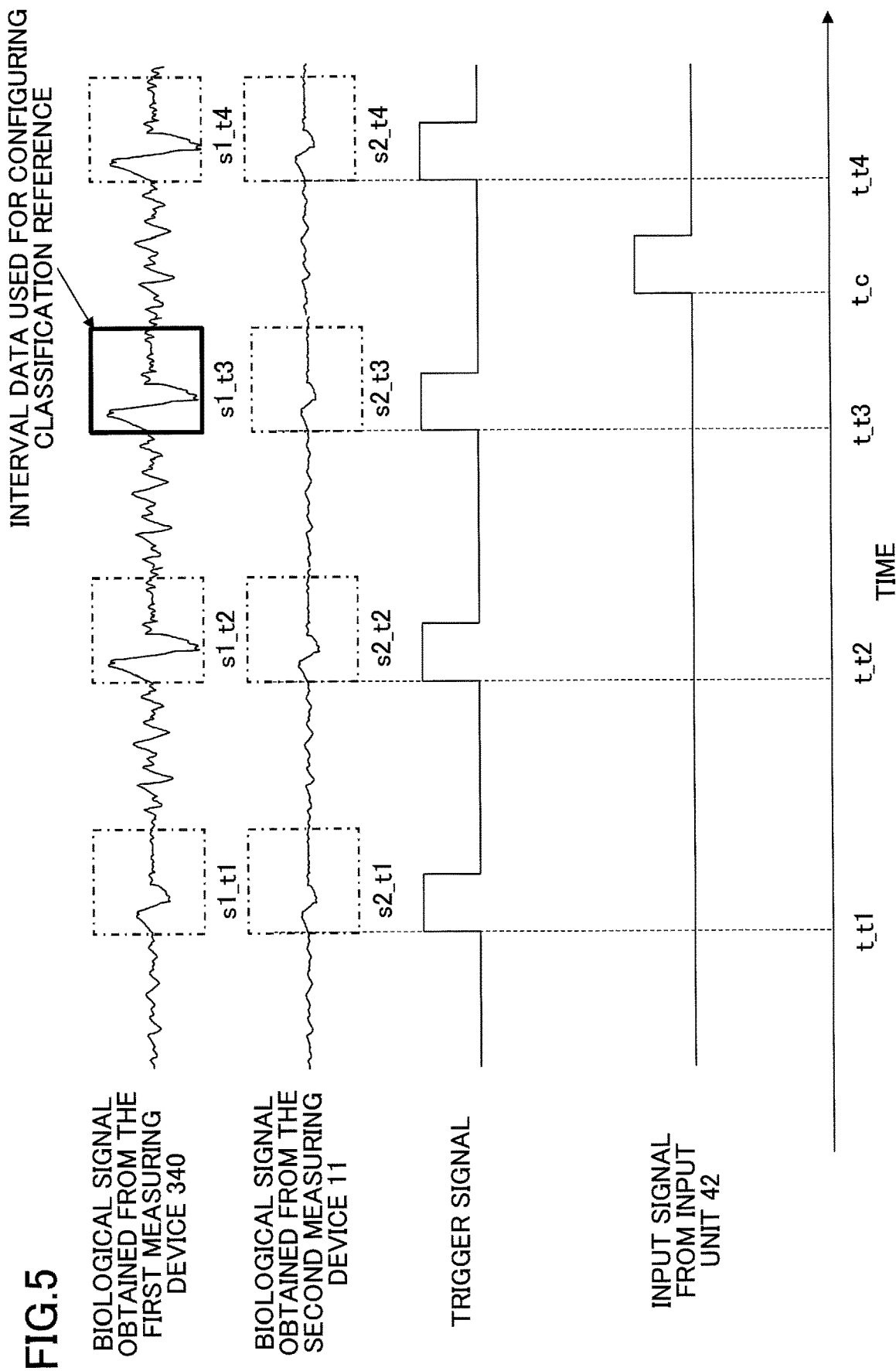
FIG. 5 is a diagram illustrating details of steps S101, S102, S103, and S104 of FIG. 4.

FIG. 5 is a diagram illustrating the details of steps S101, S102, S103, and S104 of FIG. 4. Time-series data (hereinafter, referred to as interval data) of the specific intervals indicated by s1_t1, s1_t2, s1_t3, s1_t4, s2_t1, s2_t2, s2_t3, and s2_t4 are generated by the time-series data of the biometric information obtained from the first measuring device 340 and the second measuring device 11 and by the trigger signal. For example, the time-series data of the biometric information obtained from the first measuring device 340 is the data of the myoelectric potential, and the time-series data of the biometric information obtained from the second measuring device 11 is the data of the induced magnetic field.

Each time the interval data is newly generated, the content displayed in the display unit 41 is updated. In the example shown in FIG. 5, the interval data generated immediately before the rise time of the input signal from the input unit 42 is used as the interval data used for the classification reference setting. In this case, for example, when the signal from the input unit 42 is received at time t_c (t_t3<t_c<t_t4), the interval data s1_t3 generated at time t_t3 is used to configure the classification reference. The interval data obtained from the second measuring device 11 is not used for configuring the classification reference.

Each time the calculation device 40 determines the interval data based on the trigger signal, the calculation device 40 transmits the display data for causing the display unit 41 to display the waveform of the interval data to the display unit 41. Each time the display unit 41 receives the display data, the display unit 41 updates the displayed waveform. An operator operating the computer device including the calculation device 40 observes the waveform updated in the period of the trigger signal and selects the waveform by operating the input unit 42 when the waveform suitable for configuring the classification reference is displayed. The input unit 42 outputs an input signal to the calculation device 40 based on an operation by an operator. As described above, the calculation device 40 selects the interval data generated in synchronization with the trigger signal generated immediately before the input signal as the interval data used for setting the classification reference.

Figure 6:
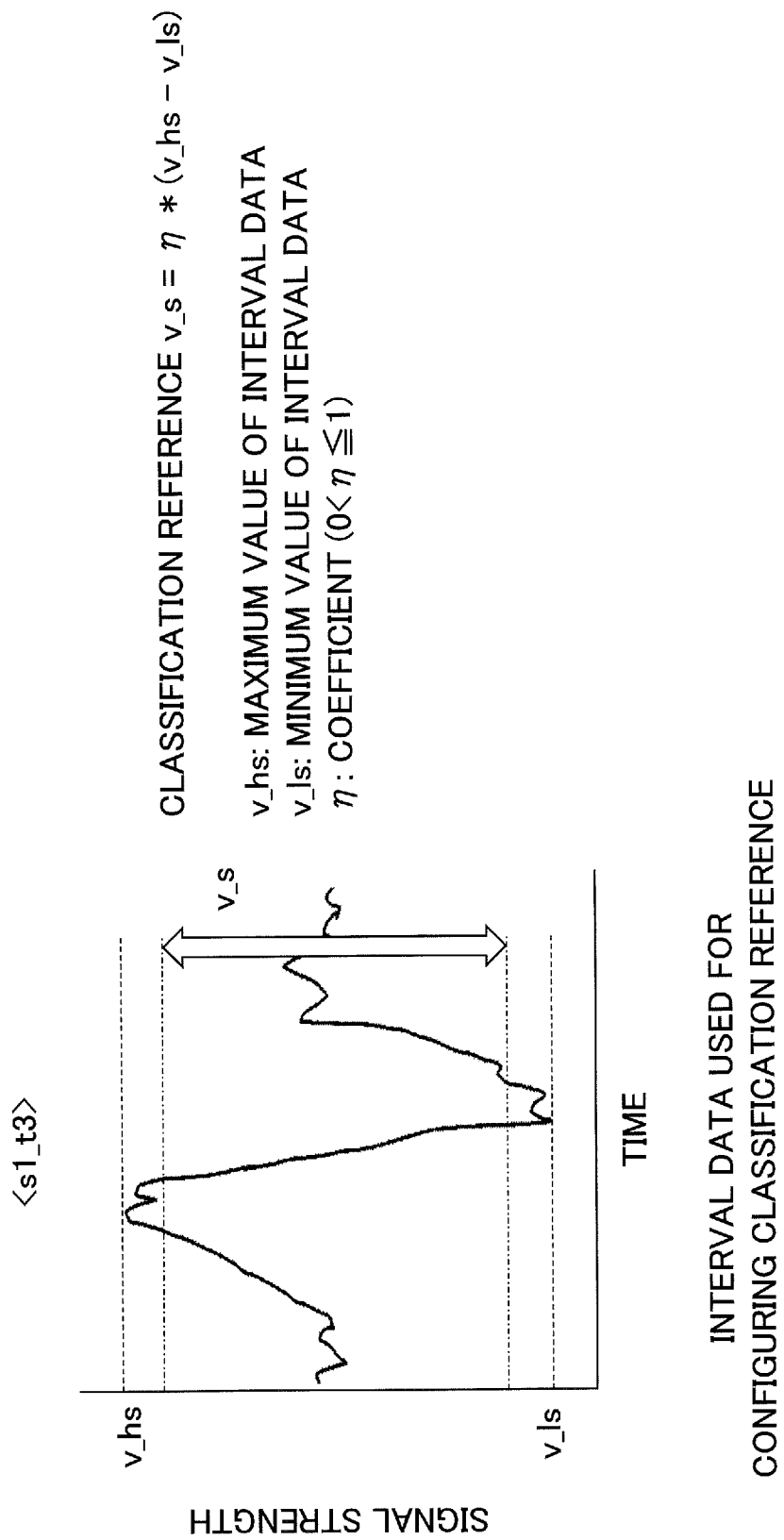
FIG. 6 is a diagram illustrating details of step S104 of FIG. 4.

FIG. 6 is a diagram illustrating the details of step S104 of FIG. 4. FIG. 6 illustrates an example of configuring a classification reference based on the interval data s1_t3 in FIG. 5. The classification reference is determined based on a characteristic value calculated from the interval data. When the difference between the maximum value and the minimum value of the interval data is used as the characteristic value, the classification reference v_s is calculated by formula (1). The sign "*" in the formula indicates a multiplication. Here, the difference between the maximum value and the minimum value corresponds to the maximum amplitude within the interval data, and the classification reference v_s corresponds to the reference amplitude.

$$\text{The classification reference } v\_s = \eta * (v\_hs - v\_ls) \quad (1)$$

η: coefficient (0<η≤1)
v_hs: Maximum value of interval data
v_ls: Minimum value of interval data
As a characteristic value for configuring a classification reference, in addition to the difference between the maximum and minimum values, a mean value, variance, signal strength of a specific frequency component, or a calculation result from models learned by the neural network, etc., may be used.

Figure 7:
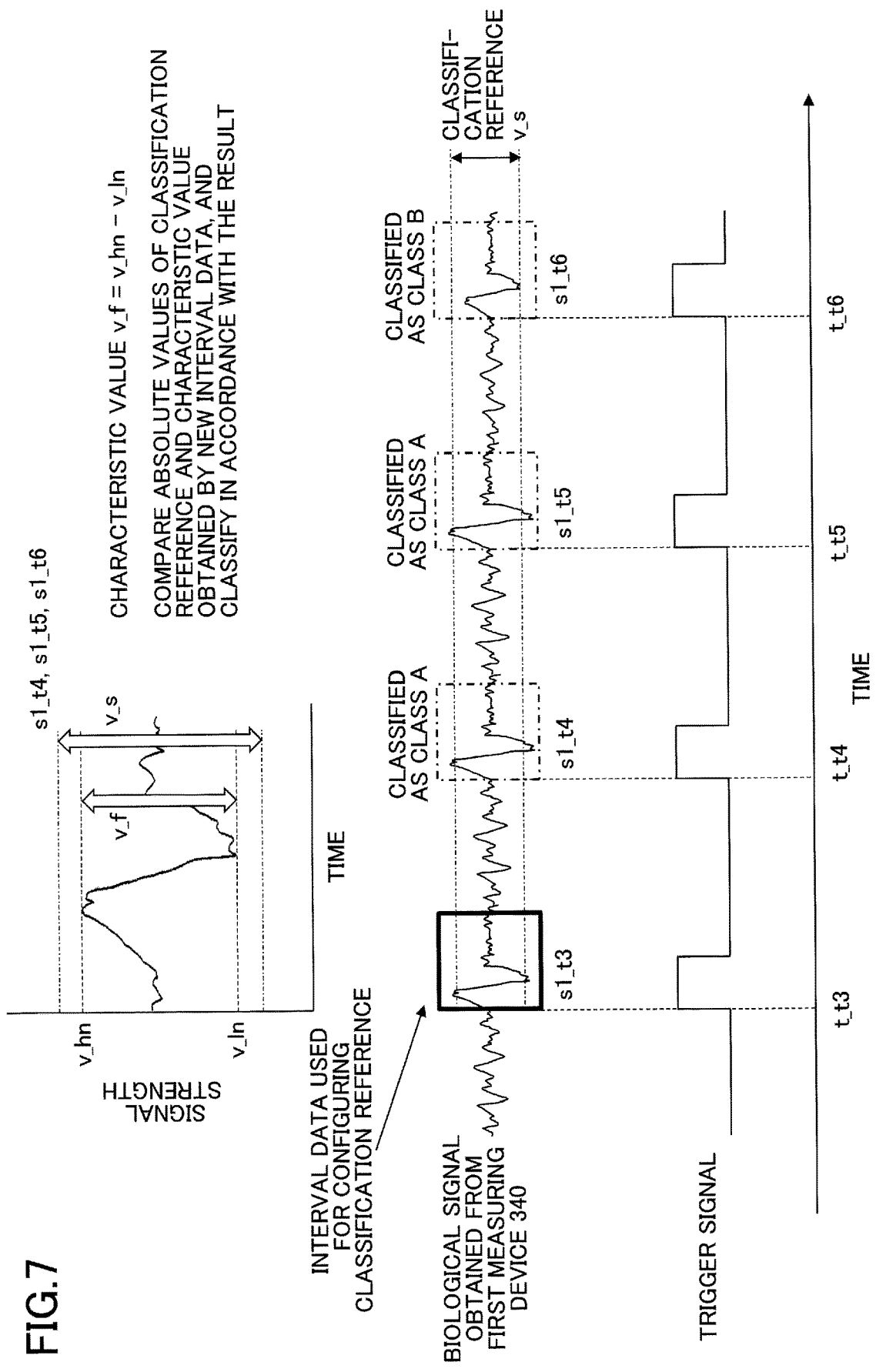
FIG. 7 is a diagram illustrating details of steps S105, S106, and S107 of FIG. 4.

FIG. 7 is a diagram illustrating the details of steps S105, S106, and S107 of FIG. 4. The interval data items (e.g., s1_t4, s1_t5, s1_t6) generated after configuring the classification reference are the interval data items to be classified. The interval data items to be classified are classified by comparing the characteristic value calculated from each interval data item with the classification reference v_s. When the difference between the maximum value and the minimum value of the interval data is used as the characteristic value, the characteristic value v_f is calculated by formula (2).

$$\text{Characteristic value } v\_f = v\_hn - v\_ln \quad (2)$$

v_hn: Maximum value of interval data
v_ln: Minimum value of interval data
Each interval data is classified into Class A if the characteristic value v_f is greater than classification reference v_s, and into Class B if the characteristic value v_f is less than or equal to classification reference v_s. The upper-left waveform of FIG. 7 is classified into Class B.

As described below, the interval data obtained from the second measuring device 11 corresponding to the interval data classified into Class A is extracted as the target data for adding and averaging. In contrast, the interval data obtained from the second measuring device 11 corresponding to the interval data classified into Class B is excluded from the target data for adding and averaging.

Since the SQUID sensor array 11, which is an example of the second measuring device 11, has a plurality of magnetic sensors (multi-sensors) disposed at positions adjacent to each other, multiple items of interval data can be obtained by a single measurement. For example, the calculation device 40 can calculate an arithmetic mean of the interval data items classified into Class A for each magnetic sensor, and the calculation device 40 can provide arithmetic mean results for respective magnetic sensor to the display unit 41. As a result, an operator can select the optimum arithmetic mean result from the plurality of arithmetic mean results, as the data used for diagnosis, etc.

In addition to the difference between the maximum value and the minimum value, a mean value, variance, signal strength of a particular frequency component, a result of calculation by a model learned by a neural network, etc., may be used as a characteristic value in the classification process. Note that the parameter used for calculating the characteristic value $v\_f$ may preferably be the same type as the type of the parameter used for calculating the classification reference $v\_s$.

In the process of step S106 of FIG. 4, the biometric information obtained from the second measuring device 11 is classified based on the classification result of the interval data obtained from the first measuring device 340. Each interval data item obtained from the first measuring device 11 is classified into a Class that is the same as the classification result of each interval data item obtained from the first measuring device 340. However, new classes may be created, and the interval data items obtained from the first measuring device 11 may be classified into the created new classes.

In the process of step S108 of FIG. 4, a plurality of interval data items obtained from the second measuring device 11 that is classified into the same class is averaged.

Figure 8:
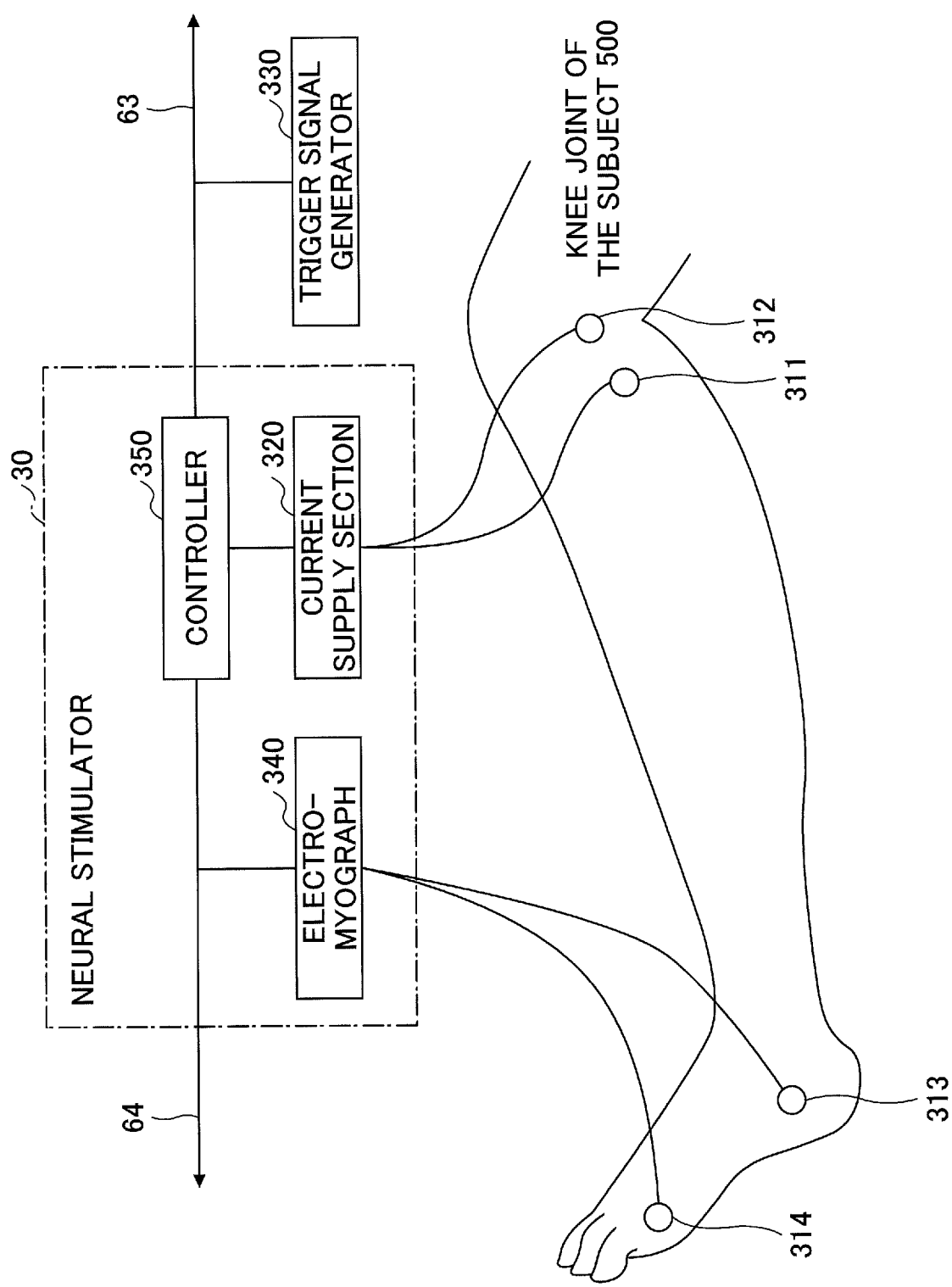
FIG. 8 is a schematic diagram illustrating a situation in which an electrode of a nerve stimulator is attached to a knee joint of a subject.

FIG. 8 is a schematic diagram exemplifying a situation in which the electrodes 310 (311, 312, 313, 314) of the neural stimulator 30 are attached to a knee joint of the subject 500. Electrode 310 is disposed, for example, in contact with the skin of subject 500. The stimulating cathode 311 and stimulating anode 312 are positioned to electrically stimulate the peroneal nerve and induce neural activity when an electric current is supplied from the current supply section 320. The detection cathode 313 and the detection anode 314 are positioned to detect the action potential of the muscle innervated by the peroneal nerve. As described above, in this example, the action potential of the muscle innervated by the peroneal nerve to be induced can be measured to determine whether neural activity is properly induced by electrical stimulation.

FIG. 9 is a diagram illustrating an example of the result of the biometric information processing according to the embodiment. Electrical stimulation (duration: 0.3 ms, stimulation frequency: 5 Hz) with the electrode 310 arranged as illustrated in FIG. 8 is an example of measuring a nerve-induced magnetic field in the lumbar spine (e.g., the number of times of averaging is 4000).

Figure 9C:
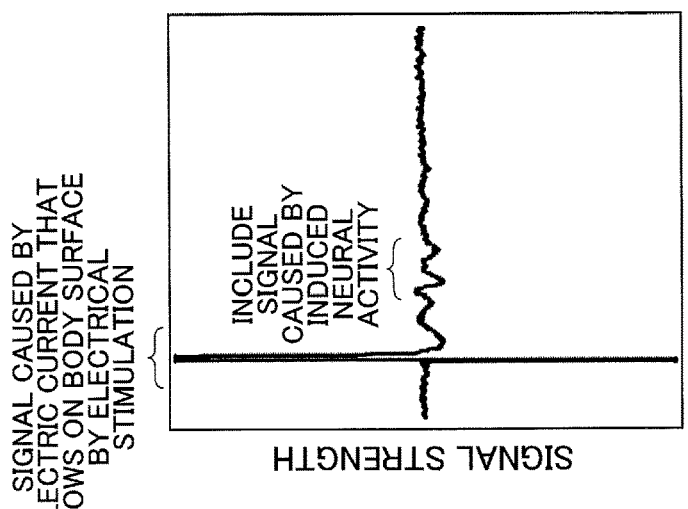
FIGS. 9A through 9C are diagrams illustrating examples of biometric information processing results according to an embodiment.
Figure 9B:
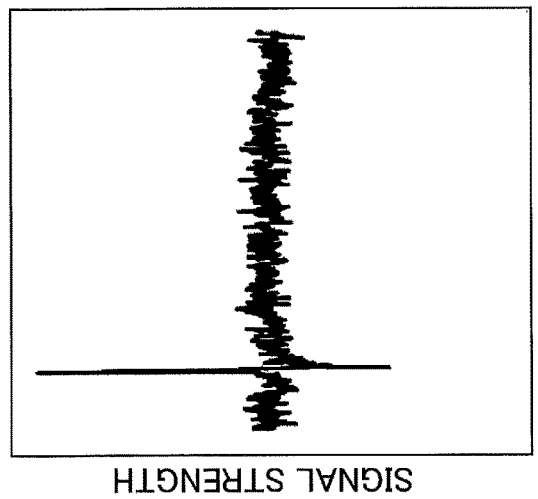
Figure 9A:
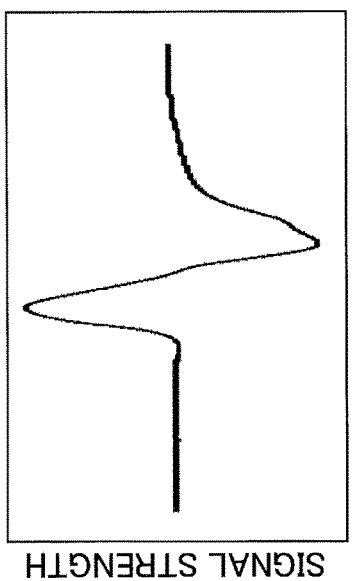

FIG. 9A is an example of the interval data obtained from electromyography 340 and used to configure a classification reference. An operator of the spinal cord induced magnetic field measuring system 1 operates the input unit 42 at a timing at which the amplitude of the myoelectric potential is sufficient, i.e., at a timing of determining that neural activity is properly induced by electrical stimulation, while looking at the display unit 41. The calculation device 40 that receives the input signal from the input unit 42 based on the operation performs the process of determining the classification reference.

FIG. 9B is an example of the waveform of the interval data obtained from the SQUID sensor array 11 (the second measuring device). Since the SN ratio is low, it is difficult to use only FIG. 9B as effective biometric information.

FIG. 9C is an example of the arithmetic mean result of the plurality of interval data items classified into Class A obtained from the SQUID sensor array 11. The calculation device 40 configures the classification reference when an operator confirms that a target to be measured is in a suitable condition for measurement based on the high signal quality biometric information, such as the biometric information illustrated in FIG. 9A. Even if it is difficult to determine whether the signal quality is favorable with single-interval data as shown in FIG. 9B, by averaging only the biometric information classified into Class A that is suitable for the arithmetic mean method as illustrated in FIG. 9C, the noise can be reduced and the effective signal can be visually recognized.

FIGS. 10A and 10B are diagrams illustrating examples of displaying the classification result. FIG. 10A illustrates a change in the classification result. As a result of the processing in step S107 of FIG. 4, the characteristic value of the interval data items classified into Class A among the interval data items measured by the second measuring device 11 is displayed by the display unit 41 as illustrated in FIG. 10A.

For example, as illustrated in FIG. 4, when the process of step S107 is performed before determining the measurement termination condition, the characteristic value is displayed by the display unit 41 one by one each time the interval data is classified into Class A. In contrast, when the process of Step S107 is performed after determining the measurement termination condition of FIG. 4, the characteristic value of all the interval data items classified into Class A is displayed by the display unit 41 at once.

FIG. 10B is a diagram illustrating a waveform obtained by superposing all the interval data items classified into Class A among the interval data items generated by the first measuring device 340. For example, the calculation device 40 causes the display device 41 to display the superposed waveform of FIG. 10B together with a signal waveform of the interval data classified in step S107 of FIG. 4.

By displaying various types of information illustrated in FIGS. 10A and 10B by the display unit 41, an operator can determine whether a measurement target can maintain a condition suitable for measurement during measurement. In addition, certainty of the measurement can be shown to a person other than the operator performing the measurement. In addition, an operator can stop the measurement upon determining that the biometric information is not suitable for neuromagnetic field measurement based on a characteristic value of the classified interval data or a superposed waveform of the interval data. In addition, the operator can stop the measurement when it is determined that the measurement of the neuromagnetic field is unsuitable based on the characteristic quantity of the classified interval data or the superimposed waveform of the interval data. For example, the measurement can be stopped (i.e., calculation of the arithmetic mean can be stopped) by selecting, by an operator, a stop button displayed on the display unit 41 using a mouse.

The calculation device 40 may stop the measurement when the interval data (Class B) with a characteristic value that is less than the classification reference is consecutively classified a predetermined number of times. For example, the predetermined number of times may be input, in advance, to the calculation device 40 by an operator operating the input unit 42. For example, in FIG. 10A, when the predetermined number of times of stopping the measurement is set to four times, when FIG. 10A is displayed, that is, when the characteristic value of Class B is consecutively displayed four times, the calculation device 40 may stop the measurement. At this time, the calculation device 40 may cause the display unit 41 to display information indicating that the measurement has been stopped.

By the above-described process, the biometric information suitable for arithmetic mean method can be classified using a classification reference that is configured upon confirming, by an operator, signal quality based on a condition of a measurement target. The arithmetic mean process can be performed after excluding biometric information that is not suitable for measurement. As a result, the effect of noise can be suppressed and a favorable biometric information processing result can be obtained.

As described above, according to the first embodiment, by configuring a classification reference using a first biometric information item (e.g., myoelectric potential) with which the classification reference can be easily configured, accuracy of data recording of a second biometric information item (e.g., neuromagnetic) can be enhanced.

Since a classification reference is configured based on a waveform visually observed by an operator, an optimum classification reference can be configured according to a measurement target. Furthermore, by obtaining an arithmetic mean of interval data items of a neuromagnetic field, noise included in a waveform of the neuromagnetic field can be reduced, and accuracy of data recording can be enhanced.

The SQUID sensor array 11 having a plurality of magnetic sensors (multi-sensors) can obtain a plurality of interval data items in a single measurement, and a plurality of arithmetic mean results can be obtained. Since it is possible to obtain data with a large amount of information, accuracy of data recording can be enhanced.

By displaying a history and a change in a state of a measurement target, such as a classification result, an operator can recognize a degree of certainty of the data acquisition. For example, an operator can determine whether measurement should be continued. If it is not suitable to continue the measurement, the operator can stop the measurement. Furthermore, if it is not suitable to continue the measurement, the calculation device 40 can automatically interrupt the measurement. Accordingly, it is possible to prevent a measurement result in a state which is not suitable for the measurement from being mixed into a target of averaging, and accuracy of data acquisition can be enhanced.

Second Embodiment

In the first embodiment, an example is described in which a nerve-induced magnetic field in the lumbar spine caused by knee joint stimulation is measured by the spinal cord induced magnetic field measurement system 1 using a nerve stimulator as the first measuring device and a magnetic field measuring device as the second measuring device. It is also possible to measure somatosensory induced magnetic fields in the cervical spine and carpal tunnel induced by elbow joint stimulation using a somatosensory induced magnetic field measurement system.

In the second embodiment, an example is described in which the neuromagnetic field of the carpal tunnel caused by the elbow joint stimulation is measured by the somatosensory induced magnetic field measuring system 2 having a configuration similar to the configuration of the spinal cord induced magnetic field measuring system 1 according to the first embodiment. The somatosensory induced magnetic field measuring system 2 described in the second embodiment is included in the neuromagnetic field measuring system together with the spinal cord induced magnetic field measuring system 1 described in the first embodiment, and the neuromagnetic field measuring system is included in the biometric information measuring system.

Figure 11:
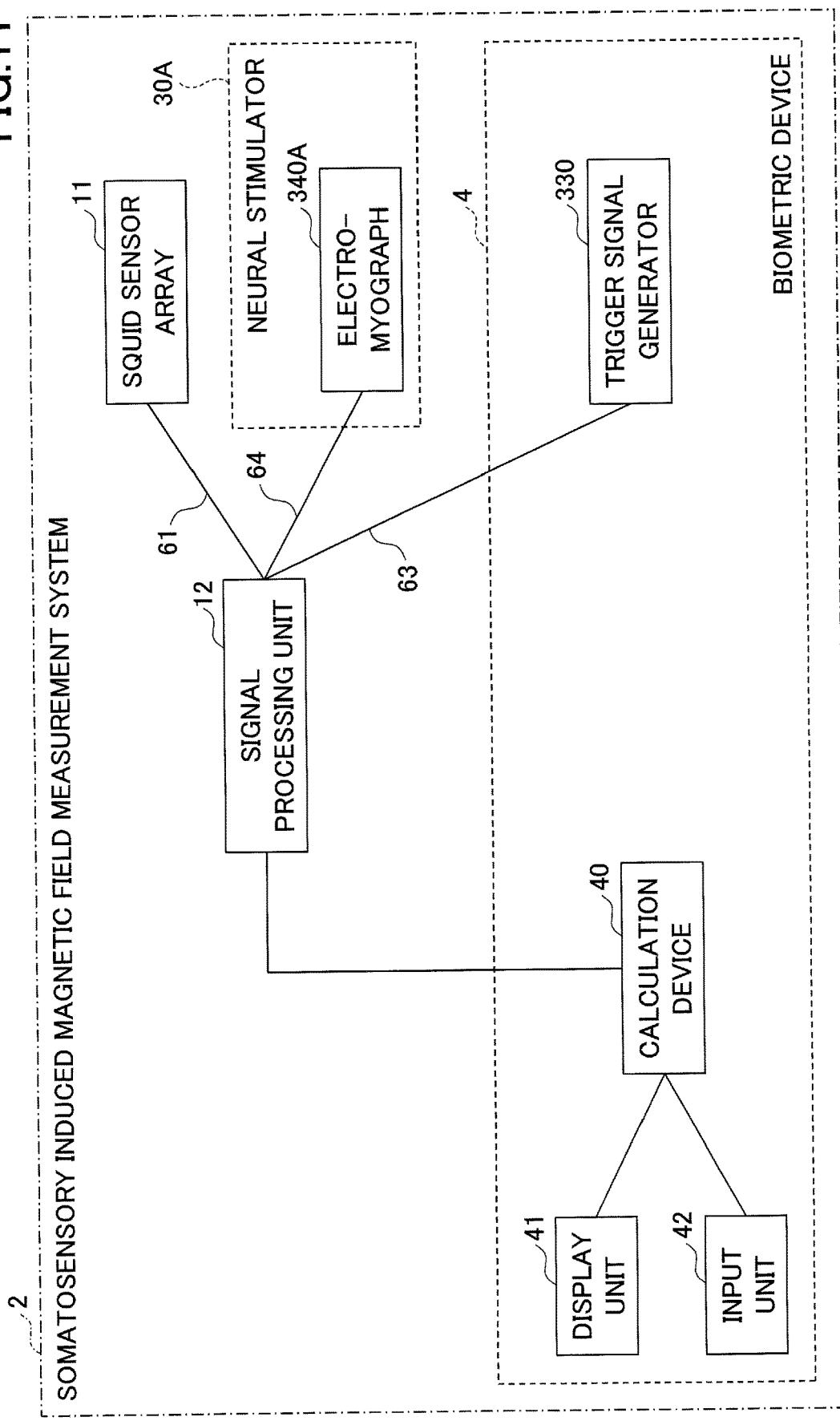
FIG. 11 is a diagram illustrating an example of a biometric device using a somatosensory induced magnetic field measurement system according to a second embodiment.

FIG. 11 is a diagram illustrating an example of a biometric apparatus using the somatosensory induced magnetic field measurement system 2 according to the second embodiment. In FIG. 11, only the components related to the embodiment are described, and other components are omitted. The somatosensory induced magnetic field measurement system 2 of the second embodiment includes the nerve stimulator 30A instead of the nerve stimulator 30 of the spinal cord induced magnetic field measuring system 1 of the first embodiment illustrated in FIG. 3. The neural stimulator 30A has an electromyograph 340A instead of an electromyograph 340. In the somatosensory induced magnetic field measurement system 2, the configuration other than the electromyograph 340A is the same as in the first embodiment. The configuration of the electromyograph 340A is described in detail in FIG. 12.

Figure 12:
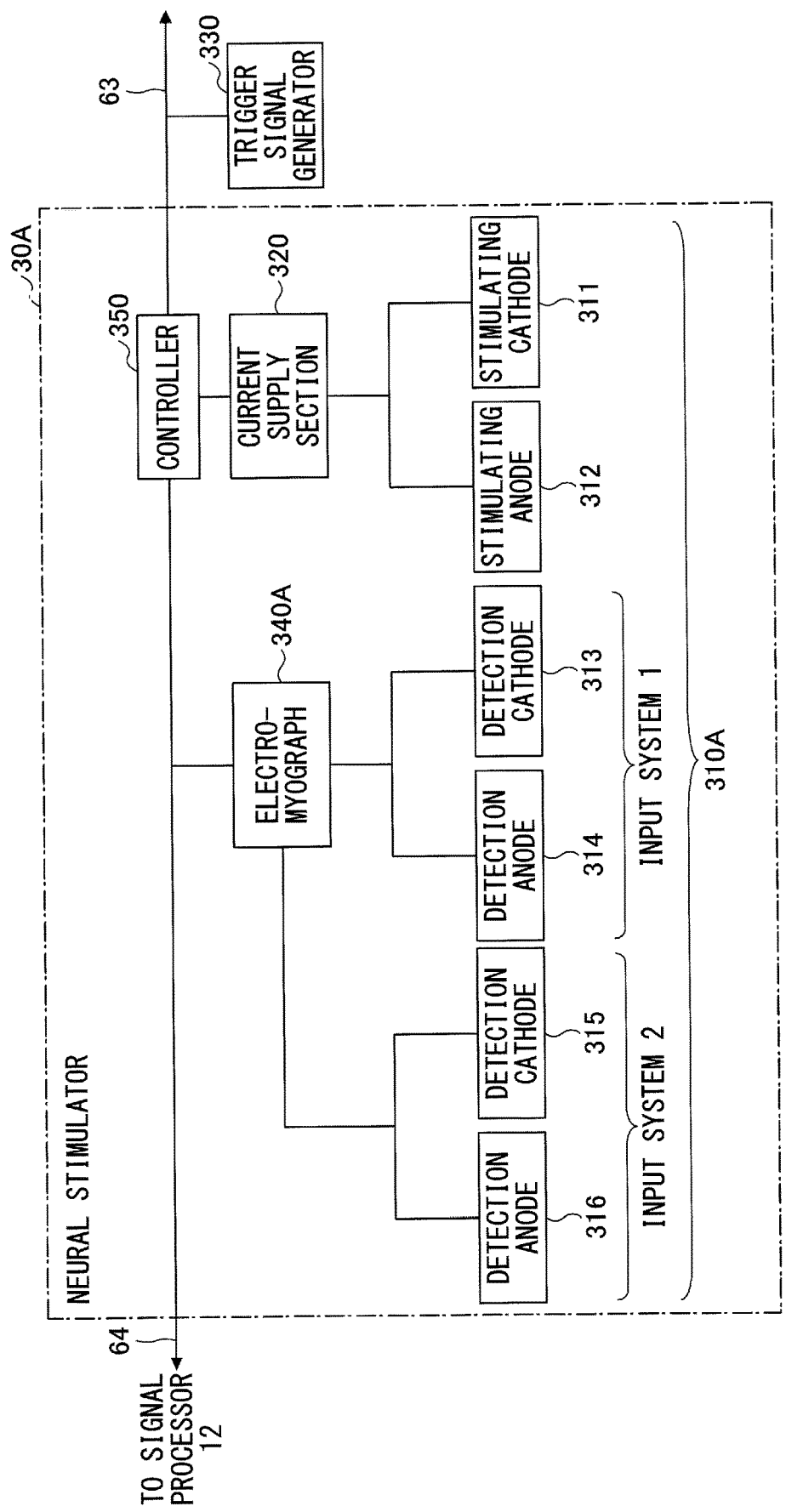
FIG. 12 is a diagram illustrating a neural stimulator including an electromyograph of FIG. 11.

FIG. 12 is a diagram exemplifying the nerve stimulator 30A including the electromyograph 340A of FIG. 11. The neural stimulator 30A is the same as the neural stimulator 30 shown in FIG. 2, except that the electrodes 310A are connected to the electromyograph 340A. Electrode 310A includes detection cathode 313, detection anode 314, as well as detection cathode 315, and detection anode 316, which are included in electrode 310 of FIG. 2. That is, the neural stimulator 30A includes two systems of detection electrodes. In the following description, the electrode pair of the detection cathode 313 and the detection anode 314 is referred to as the input system 1 of the first measuring device, and the electrode pair of the detection cathode 315 and the detection anode 316 are referred to as the input system 2 of the first measuring device.

In the following, a process in the calculation device 40 is described. The overall processing flow (FIG. 4) is similar to that of the first embodiment.

Figure 13:
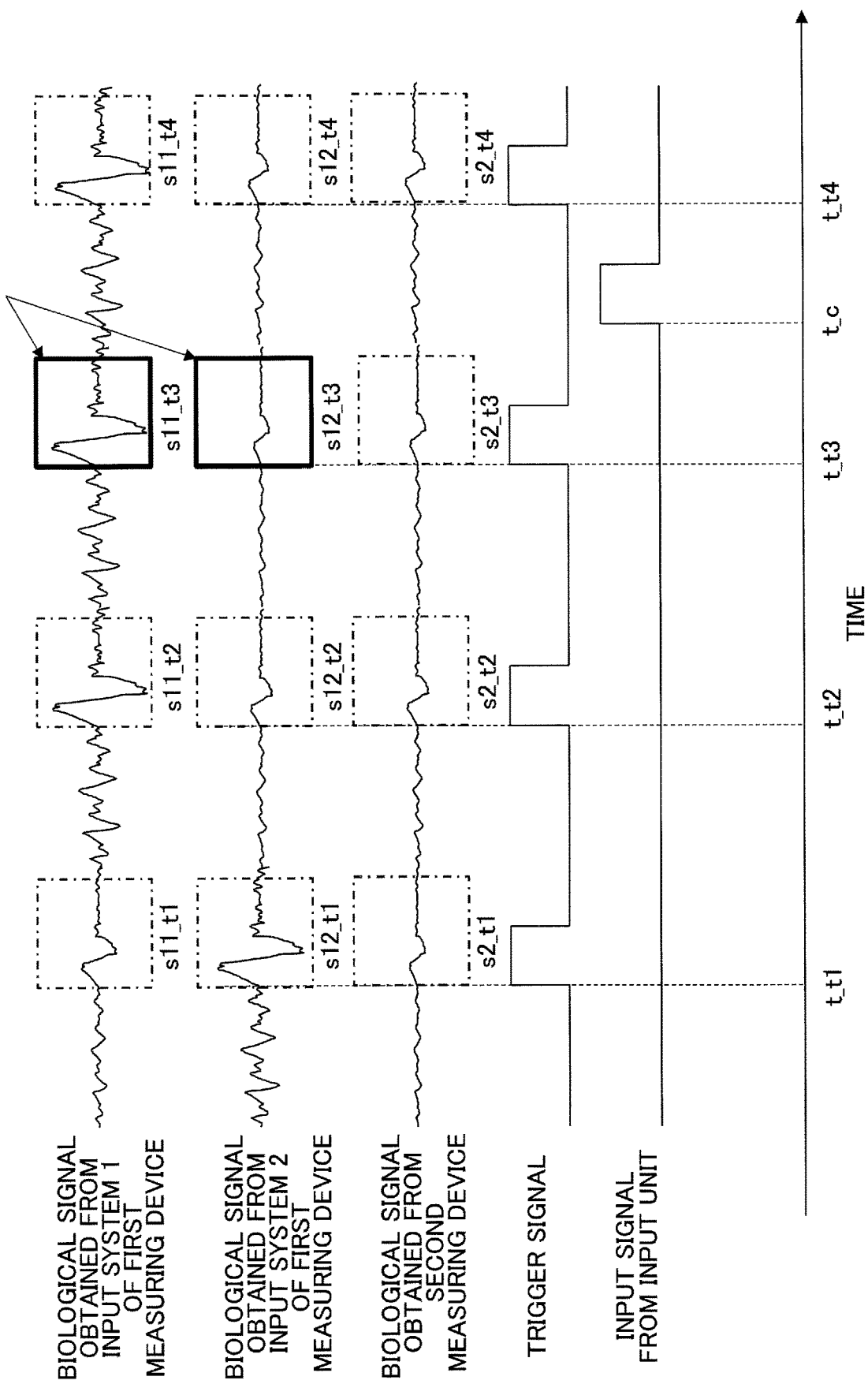
FIG. 13 is a diagram illustrating details of steps S101, S102, S103, and S104 of FIG. 4 in the calculation device of FIG. 11.

FIG. 13 is a diagram illustrating details of steps S101, S102, S103, and S104 of FIG. 4 in the calculation device 40 of FIG. 11. The time-series data in the specific intervals indicated by s11_t1, s11_t2, s11_t3, s11_t4, s12_t1, s12_t2, s12_t3, s12_t4, s2_t1, s2_t2, and s2_t3, s2_t4 (which is referred to as interval data, below) is generated by time-series data and the trigger signal obtained from the first measuring device 340 and the second measuring device 11.

Each time the interval data is newly generated, the content displayed by the display unit 41 is updated. The interval data generated immediately before the rise time of the input signal from the input unit 42 is used as the interval data used for configuration of the classification reference. In this case, for example, when the signal from the input unit 42 is received at time t_c (t_t3<t_c<t_t4), the interval data s11_t3 and s12_t3 generated at time t_t3 are used to configure the classification reference. The interval data obtained from the second measuring device 11 is not used for configuring the classification reference.

The method for calculating the classification reference in step S104 of FIG. 4 is the same as that of the first embodiment. However, the classification reference calculated on the input system 1 of the first measuring device 340 is v_s1, and the classification reference calculated on the input system 2 of the first measuring device 340 is v_s2. The method of configuring the classification reference v_s1 and v_s2 can be described by replacing the classification reference v_s in FIG. 6 with the classification reference v_s1 and v_s2, respectively.

The method of calculating the characteristic value (v_f shown in FIG. 7) in step S105 of FIG. 4 is the same as that of the first embodiment. However, the characteristic value computed for the input system 1 of the first measuring device 340 is v_f1, and the characteristic value computed for the input system 2 of the first measuring device 340 is v_f2. Each interval data after configuring the classification reference is classified into Class A if v_f1>v_s1 and v_f2<v_s2, and into Class B if v_f1 is less than or equal to v_s1 or v_f2 is greater than or equal to v_s2.

The method of determining the characteristic values v_f1 and v_f2 can be achieved by replacing the characteristic value v_f in FIG. 7 with the characteristic values v_f1 and v_f2, and replacing the classification reference v_s in FIG. 7 with the classification references v_s1 and v_s2. However, as described above, classification to Class A is made only when the characteristic value v_f1 is greater than the classification reference v_s1 and the characteristic value v_f2 is less than the classification reference v_s2 as described above.

The processing of steps S106 and S108 in FIG. 4 is the same as that of the first embodiment. The first measuring device 340 may process three or more input systems. In this case, when the characteristic values of all input systems satisfy the classification references, the calculation device 40 causes the display unit 41 to display the characteristic value of the interval data measured by the second measuring device 11 in the interval data.

Figure 14:
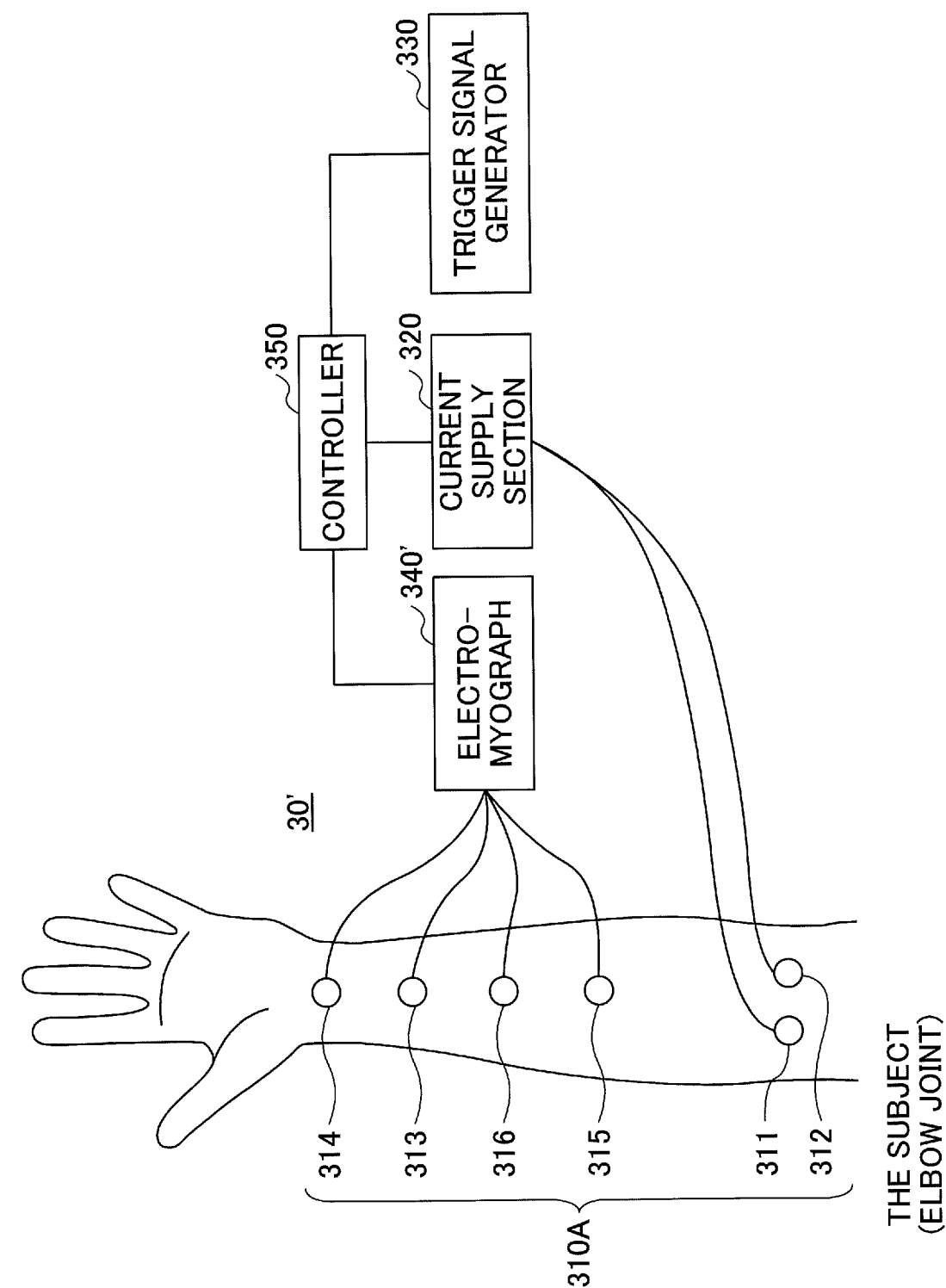
FIG. 14 is a schematic diagram illustrating a situation in which an electrode of the nerve stimulator of FIG. 12 is attached to an elbow joint of a subject.

FIG. 14 is a schematic diagram exemplifying a situation in which the electrode 310A (311, 312, 313, 314, 315, 316) of the nerve stimulator 30A is attached to the elbow joint of a subject 500. The electrode 310A is disposed, for example, in contact with the skin of subject 500. The stimulating cathode 311 and stimulating anode 312 are positioned to electrically stimulate the median nerve and induce neural activity when current is supplied from the current supply section 320.

The detection cathode 313 and the detection anode 314 are positioned to detect a complex nerve action potential of the median nerve. The detection cathode 315 and detection anode 316 are arranged to detect action potentials in muscle innervated by the median nerve. As described above, by simultaneously measuring the action potential of the muscle innervated by the nerve to be stimulated and the complex nerve action potential of the nerve, it is possible to determine whether electrical stimulation appropriately induces nerve activity and whether electrical stimulation induces muscle contraction.

Figure 15:
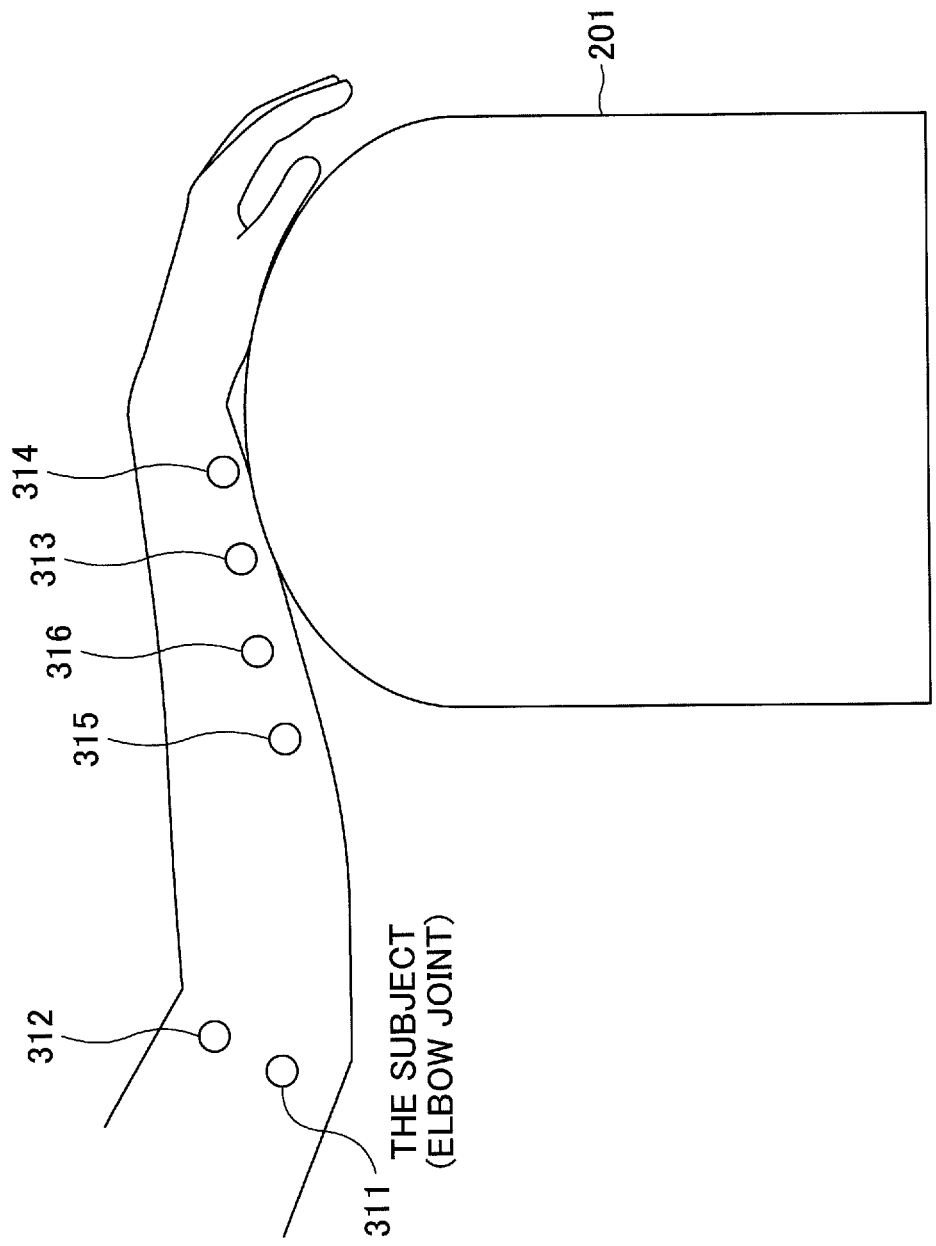
FIG. 15 is a schematic diagram illustrating a situation in which a carpal tunnel region of a subject is measured by the somatosensory induced magnetic field measurement system illustrated in FIG. 11.

FIG. 15 is a schematic diagram illustrating a situation in which the carpal tunnel of the subject 500 is measured by the somatosensory induced magnetic field measurement system 2 illustrated in FIG. 11. The carpal tunnel portion of subject 500 is brought into contact with the projection 201 of the cold container 20 to measure the neuromagnetic field. Since the position at which the electrical stimulation is applied and the region at which the magnetic field is measured are close to each other, biometric information caused by neural activity induced by electrical stimulation, as well as biometric information caused by an electric current flowing through the body surface by the electrical stimulation and muscle contraction induced by electrical stimulation can be observed in magnetic field measurement.

Accordingly, it is desirable to electrically stimulate in the measurement of the neuromagnetic field in the carpal tunnel so that neural activity is induced and no muscle contraction is observed. For this reason, as described in FIG. 13, when the characteristic quantity v_f1 of the biological signal obtained from the input system 1 is larger than the classification reference v_s1 and the characteristic quantity v_f2 of the biological signal obtained from the input system 2 is smaller than the classification reference v_s2, the biological signal is classified into Class A.

Figure 16C:
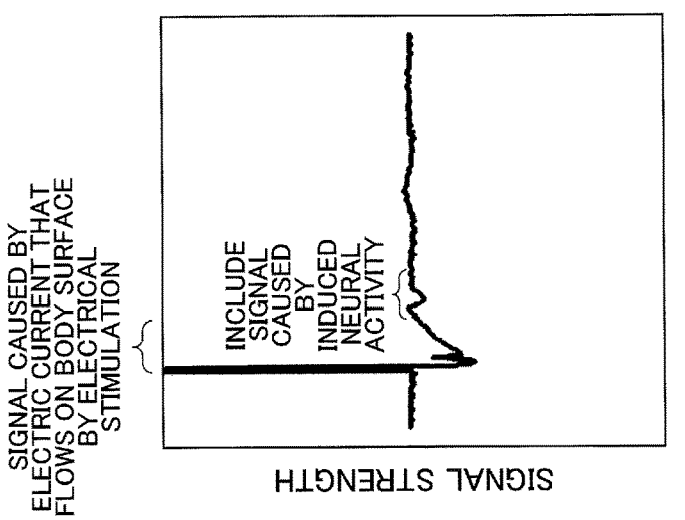
FIGS. 16A-16C are diagrams illustrating an example of a result of the biometric information processing in the biometric apparatus shown in FIG. 11.
Figure 16B:
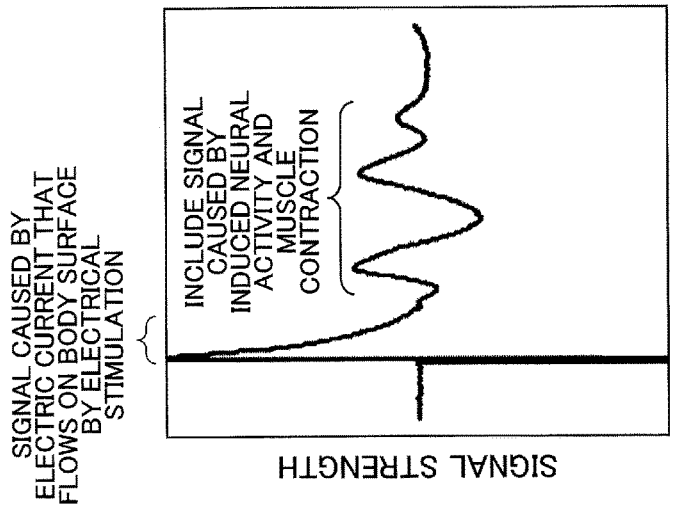
Figure 16A:
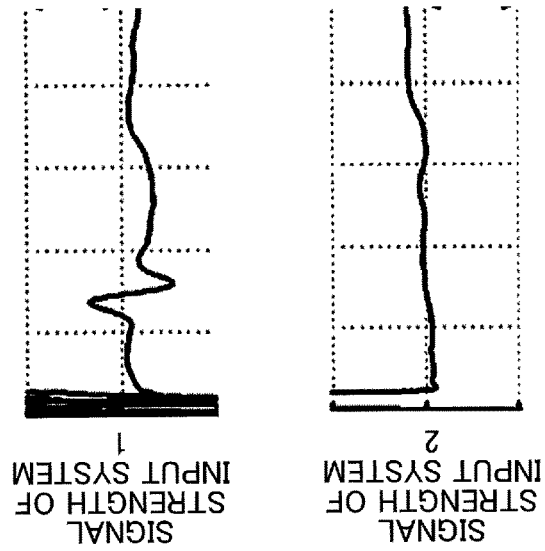

FIGS. 16A, 16B, and 16C are diagrams illustrating an example of the result of the biometric information processing result in the biometric device shown in FIG. 11. An example of the measurement of neurogenic magnetic fields in the carpal tunnel is illustrated in which by percutaneous electrical stimulation (duration: 0.3 ms, stimulation frequency: 20 Hz) is applied in the arrangement of the electrodes shown in FIG. 14 (e.g., a number of times of averaging is 2,000 times).

FIG. 16A is an example of the interval data obtained from the electromyograph 340A and used to configure the classification reference. The operator of the somatosensory induced magnetic field measuring system 2 operates the input unit 42 at a timing at which it is determined that the amplitude of the complex myoelectric potential is sufficient and the myoelectric potential is not observed while looking at the display unit 41. The calculation device 40 which receives the input signal from the input unit 42 based on the operation performs the process of determining the classification reference.

FIG. 16B is an example of the result of averaging of the 2000 interval data items obtained from the SQUID sensor array 11 (the second measuring device) without classification processing. During the process of obtaining the 2000 interval data items, the subject's contact with the stimulating electrode changes and the measurement is performed in a state including a signal caused by muscle contraction. Accordingly, it is difficult to visually identify only the signal caused by nerve activity.

FIG. 16C is an example of the averaging result of the plurality of interval data items classified into Class A obtained from the SQUID sensor array 11. Since the interval data including a signal caused by muscle contraction is excluded from the averaging by the classification process, the signal caused by neural activity can be easily visualized. The display of the classification results is the same as in the first embodiment.

As described above, in the second embodiment, an effect can be obtained that is the same as the effect of the first embodiment. Furthermore, in the second embodiment, by obtaining a plurality of biometric signals from a plurality of respective systems by the first measuring device 340, a classification reference with higher sorting performance can be configured and the accuracy of data recording can be enhanced.

Figure 17:
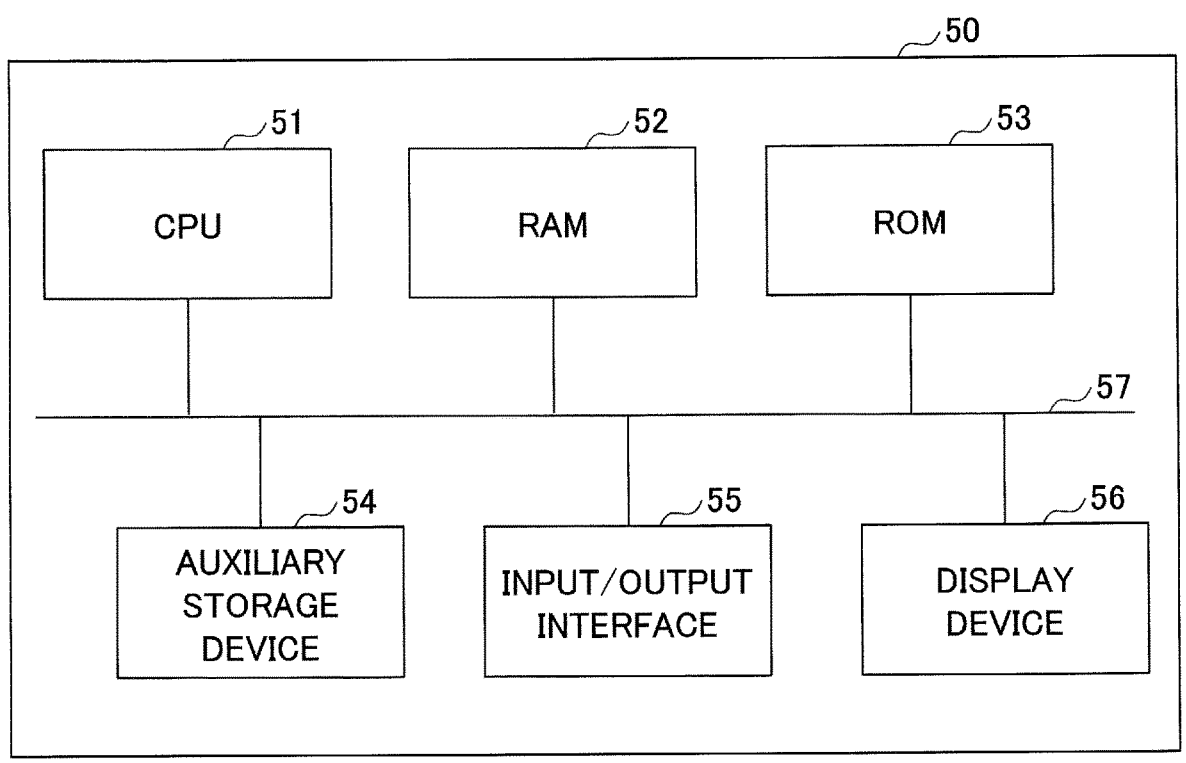
FIG. 17 is a diagram illustrating an example of a hardware configuration of a computer device including the calculation device of FIGS. 3 and 11.

FIG. 17 is a diagram illustrating an example of a hardware configuration of a computer device 50 including the calculation device 40 of FIG. 3 and FIG. 11.

The computer device 50 is, for example, an information processing device including a CPU 51; a RAM 52; a ROM 53; an auxiliary storage 54; an input/output interface 55; and a display unit 56, and these are mutually connected by a bus 57. The CPU 51 corresponds to the calculation device 40, and the display device 56 corresponds to the display unit 41.

The CPU 51 controls the overall operation of the computer device 50, and performs various types of information processing, such as the operation shown in FIG. 4. The CPU 51 executes a biometric program stored in the ROM 53 or the auxiliary storage device 54 to configure a classification reference, to classify data of a specific interval using the classification reference, to cause the display unit 56 to display the measured waveform, etc.

The RAM 52 is used as a work area of the CPU 51 and may include a non-volatile RAM for storing a biometric program and information. The ROM 53 stores various types of programs and parameters used in programs. The biometric program according to the embodiments may be stored in the ROM 53.

The auxiliary storage device 54 is a storage device, such as an SSD (Solid State Drive) or an HDD (Hard Disk Drive). The auxiliary storage device 54 stores, for example, a control program, such as an OS (Operating System) for controlling the operation of the computer device 50, or various types of data and files required for the operation of the computer device 50.

The input/output interface 55 includes a user interface, such as a touch panel, keyboard, operation buttons, speakers, and communication interface for communicating with other electronic devices. The display device 56 displays the waveform of each specific interval illustrated in FIG. 5, the waveforms, etc., illustrated in FIG. 9A and FIG. 9C, or FIG. 16 A and FIG. 16C. In the display device 56, a selection button is displayed, which is to be selected by an operator using a mouse when a waveform suitable for configuring a classification reference is displayed on the display unit 56.

Figure 18:
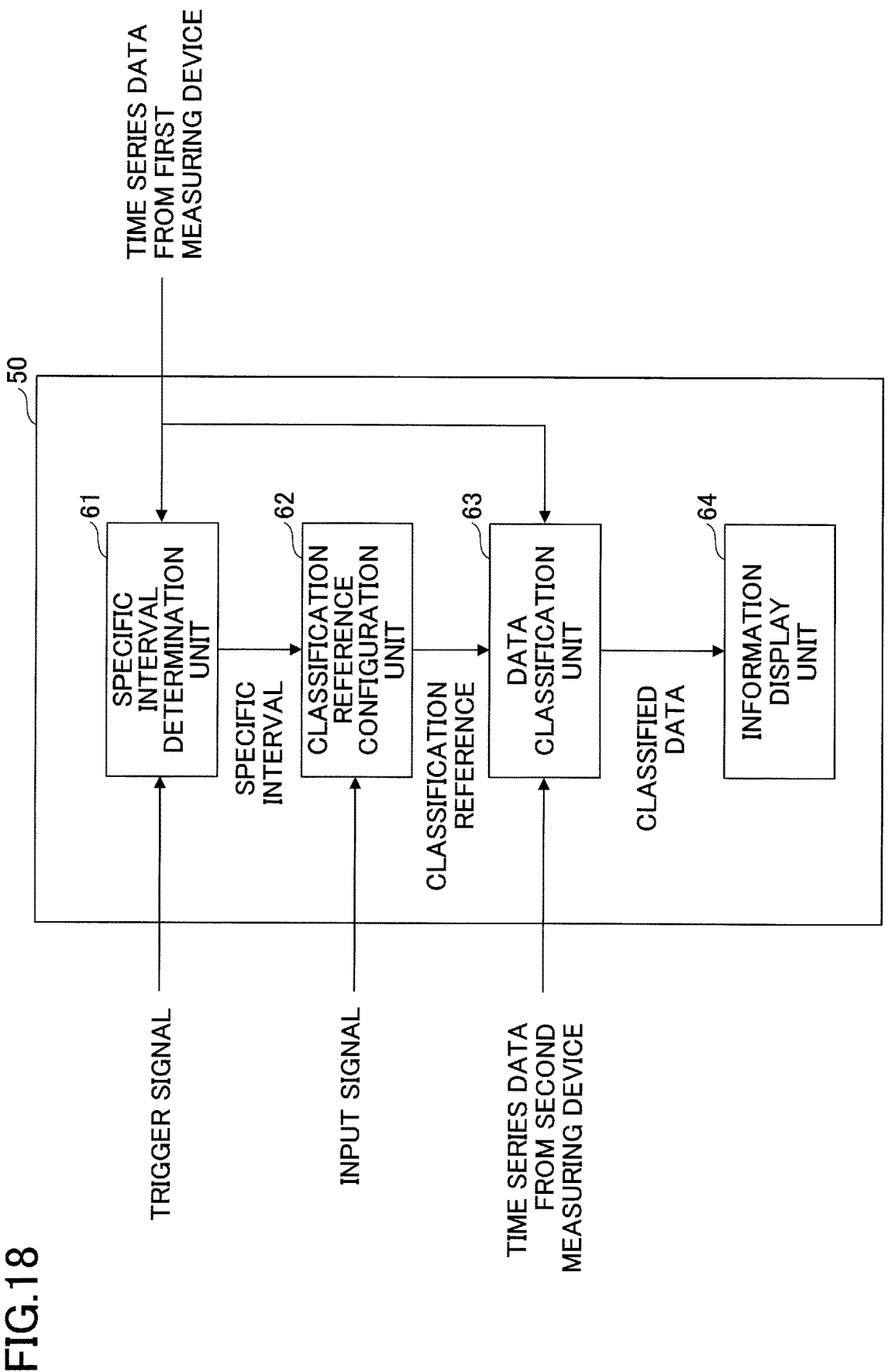
FIG. 18 is a functional block diagram of a computer device 50 including the calculation device 40 of FIGS. 3 and 11.

FIG. 18 is a functional block diagram of the computer device 50 including the calculation device 40 according to FIG. 3 or FIG. 11.

The computer device 50 includes a specific interval determination unit 61; a classification reference configuration unit 62; a data classification unit 63; and an information display unit 64. For example, the specific interval determination unit 61, the classification reference configuring unit 62, the data classification unit 63, and the information display unit 64 are implemented by executing the biometric program by the calculation device 40.

As described in FIG. 5, the specific interval determination unit 61 determines a specific interval in the time series data in response to a trigger signal output from the trigger signal generator 330. For example, the specified interval determination unit 61 performs the processing of step S102 of FIG. 4.

As described in FIG. 6, the classification reference configuration unit 62 configures a classification reference for classifying the time series data of the specific interval using the time series data of the specific interval while using an input signal from the input unit 42 as a trigger. For example, the classification reference configuration unit 62 executes the process of step S104 of FIG. 4.

As described in FIG. 7, the data classification unit 63 classifies the time-series data from the first measuring device 340 based on the classification reference configured using the time-series data from the first measuring device 340. The data classification unit 63 classifies data in the specific interval of the time-series data of the second measuring device 11 by using the classification results. For example, the data classification unit 63 performs the process of steps S105 and S106 of FIG. 4.

The information display unit 64 corresponds to the process of step S109 of FIG. 4. The information display unit 64 displays a result of classifying the data on the display unit 41.

The display unit 41 (the display device 56) that displays a classification result may be one or more display devices. For example, a display device that is referred to by an operator upon input from the input unit 42 and the display device displaying the result of the classification may be different devices.

The embodiments of the present invention are not limited to the measuring device described in the first embodiment and the second embodiment. The embodiments of the present invention may be applied to a method in which stimulation is input and measurement is performed.

Although the present invention is described above based on the embodiments, the present invention is not limited to the above-described embodiments. The embodiments may be modified within a scope of the gist of the present invention, and the embodiments may be suitably defined according to an application.

The present application is based on and claims the benefit of priority of Japanese priority application No. 2019-047690 filed on Mar. 14, 2019, the entire content of which is hereby incorporated herein by reference.

What is claimed is:

1. A biometric apparatus comprising:
 a calculation device that processes first time series data from a first measuring device that measures biometric information and second time series data from a second measuring device that measures biometric information that differs from the biometric information measured by the first measuring device;
 a display device that displays the time series data;
 a trigger signal generator that generates one or more trigger signals; and
 an input unit that receives an operation by an operator,
 wherein the calculation device determines one or more specific intervals of the first time series data based on the one or more trigger signals output from the trigger signal generator,
 wherein the calculation device configures a classification reference for classifying time series data in the one or more specific intervals using the time series data in a first specific interval of the one or more specific intervals, while using an input signal from the input unit as a trigger,
 wherein the calculation device classifies the second time series data for the one or more specific intervals using a result of classifying the first time series data based on the configured classification reference, and
 wherein the calculation device causes the display unit to display a classification result of the second time series data.

2. The biometric apparatus according to claim 1, wherein the time series data is waveform data, and
 wherein the calculation device configures a reference amplitude that is the classification reference based on a maximum amplitude of the waveform data in the first specific interval of the one or more specific intervals determined by the input signal as the trigger, in the waveform data in the one or more specific intervals obtained from the first measuring device by measurement, and
 wherein, upon determining that an amplitude of the waveform data in a second specific interval of the one or more specific intervals obtained by the first measuring device by the measurement exceeds the reference amplitude, the calculation device classifies the waveform data obtained by the second measuring device by measurement in the second specific interval of the one or more specific intervals as valid data.

3. The biometric apparatus according to claim 1, wherein the calculation device includes a function to calculate an arithmetic mean of the time series data in the plurality of specific intervals classified into an identical class.

4. The biometric apparatus according to claim 1, wherein the calculation device processes a plurality of time series data items of a respective plurality of systems from the first measuring device, and the calculation device configures a classification reference for classifying the time series data in the one or more specific intervals using the plurality of time series data items of the respective plurality of systems in the one or more specific intervals.

5. The biometric apparatus according to claim 4, wherein the time series data is waveform data, and
wherein the calculation device configures, for each of the plurality of systems, a reference amplitude that is the classification reference based on a maximum amplitude of waveform data in the first specific interval of the one or more specific intervals determined by the input signal as the trigger, in the waveform signal in the one or more specific intervals obtained by the first measuring device by measurement, and
wherein, upon determining, for each of the plurality of systems, that an amplitude of the waveform data in a second specific interval of the one or more specific intervals obtained by the first measuring device by the measurement exceeds the reference amplitude, the calculation device classifies the waveform data obtained by the second measuring device by measurement in the second specific interval of the one or more specific intervals as valid data.

6. The biometric apparatus according to claim 1, wherein the calculation device processes time series data items of a respective plurality of systems from the second measuring device.

7. The biometric apparatus according to claim 3, wherein the calculation device classifies whether time series data in each of the one or more specific intervals sequentially determined after configuring the classification reference is to be averaged,
wherein, upon determining that the time series data in one of the one or more specific intervals sequentially determined after configuring the classification reference is classified to be averaged, the calculation device updates an averaging result, and
wherein, upon determining that the time series data in one of the one or more specific intervals sequentially determined after configuring the classification reference is classified not to be averaged once or more times continuously, the calculation device stops calculation of averaging.

8. The biometric apparatus according to claim 1, wherein the calculation device includes a display device that displays a classification result and a waveform of the time series data in each of the one or more specific intervals.

9. The biometric apparatus according to claim 1, wherein the time series data measured by the first measuring device is data of muscle potential generated in a living body to be measured, and
wherein the time series data measured by the second measuring device is data of an induced magnetic field generated in the living body in response to stimulation.

10. The biometric apparatus according to claim 9, further comprising:
a stimulating part that provides electric stimulation to the living body to be measured,
wherein the first measuring device measures data of muscle potential generated in the living body in response to the electric stimulation, and
wherein the second measuring device measures data of an induced magnetic field generated in the living body in response to the electric stimulation.

11. A biometric system comprising:
a first measuring device that measures biometric information and that generates first time series data;
a second measuring device that measures biometric information that differs from the biometric information measured by the first measuring device and that generates second time series data;
a calculation device that processes the first time series data from the first measuring device and the second time series data from the second measuring device;
a display device that displays the time series data;
a trigger signal generator that generates one or more trigger signals; and
an input unit that receives an operation by an operator,
wherein the calculation device determines one or more specific intervals of the first time series data in response to the one or more trigger signals output from the trigger signal generator,
wherein the calculation device configures, using the time series data in a first specific interval of the one or more specific intervals, a classification reference for classifying the time series data in the one or more specific intervals while using an input signal from the input unit as a trigger signal,
wherein the calculation device classifies, using a result of classifying the first time series data based on the configured classification reference, the second time series data in the one or more specific intervals, and
wherein the calculation device causes the display device to display a result of classifying the second time series data.

12. The biometric system according to claim 11, wherein the time series data is waveform data,
wherein the calculation device configures a reference amplitude that is the classification reference based on a maximum amplitude of the waveform data in the first specific interval of the one or more specific intervals determined by the input signal as the trigger, in the waveform data in the one or more specific intervals obtained by the first measuring device by measurement; and
wherein, upon determining that an amplitude of the waveform data in a second specific interval of the one or more specific intervals obtained by the first measuring device by the measurement exceeds the reference amplitude, the calculation device classifies the waveform data obtained by the second measuring device by measurement in the second specific interval of the one or more specific intervals as valid data.

13. The biometric system according to claim 11, wherein the time series data is waveform data,
wherein the calculation device processes a plurality of time series data items of a respective plurality of systems from the first measuring device,
wherein the calculation device configures, for each of the plurality of systems, a reference amplitude that is the classification reference based on a maximum amplitude of the waveform data in the first specific interval of the one or more specific intervals determined by the input signal as the trigger in the wave form signal in the one or more specific intervals obtained by the first measuring device by measurement, and wherein, upon determining, for each of the plurality of systems, that an amplitude of the waveform data in a second specific interval of the one or more specific intervals obtained by the first measuring device by the measurement exceeds the reference amplitude, the calculation device classifies the waveform data obtained by the second measuring device by measurement in the second specific interval of the one or more specific intervals as valid data.

14. A biometric method executed by a biometric apparatus, the biometric apparatus including a calculation device that processes first time series data from a first measuring device that measures biometric information and second time series data from a second measuring device that measures biometric information that differs from the biometric information measured by the first measuring device, a display device that displays the time series data, a trigger signal generator that generates one or more trigger signals, and an input unit that receives an operation by an operator, wherein the biometric method comprises:
determining, by the calculation device, one or more specific intervals of the first time series data in response to the one or more trigger signals output from the trigger signal generator;
configuring, by the calculation device, a classification reference for classifying the time series data in the one or more specific intervals using the time series data in a first specific interval of the one or more specific intervals, while using an input signal from the input unit as a trigger;
classifying, by the calculation device using a result of classifying the first time series data based on the configured classification reference, the second time series data in the one or more specific intervals; and
causing, by the calculation device, the display device to display a result of classifying the second time series data.

15. The biometric method according to claim 14, wherein the time series data is waveform data, and
wherein the biometric method further comprises:
configuring, by the calculation device, a reference amplitude that is the classification reference based on a maximum amplitude of the waveform data in the first specific interval of the one or more specific intervals determined by the input signal as the trigger, in the waveform data in the one or more specific intervals obtained by the first measuring device by measurement; and
upon determining, by the calculation device, that an amplitude of the waveform data in a second specific interval of the one or more specific intervals obtained by the first measuring device by the measurement exceeds the reference amplitude, classifying, by the calculation device, the waveform data obtained by the second measuring device by measurement in the second specific interval of the one or more specific intervals as valid data.

16. The biometric method according to claim 14, wherein the time series data is waveform data, and
wherein the biometric method further comprises:
processing, by the calculation device, a plurality of time series data items of a respective plurality of systems from the first measuring device;
configuring, for each of the plurality of systems, by the calculation device, a reference amplitude that is the classification reference based on a maximum amplitude of the waveform data in the first specific interval of the one or more specific intervals determined by the input signal as the trigger, in the waveform signal in the one or more specific intervals obtained by the first measuring device by measurement; and
upon determining, for each of the plurality of systems, by the calculation device, that an amplitude of the waveform data in a second specific interval of the one or more specific intervals obtained by the first measuring device by the measurement exceeds the reference amplitude, classifying, by the calculation device, the waveform data obtained by the second measuring device by measurement in the second specific interval of the one or more specific intervals as valid data.

17. A non-transitory computer readable recording medium storing a biometric program for causing a biometric apparatus to execute a biometric method for classifying biometric information, the biometric apparatus including a calculation device that processes first time series data from a first measuring device that measures biometric information and second time series data from a second measuring device that measures biometric information that differs from the biometric information measured by the first measuring device, a display device that displays the time series data, a trigger signal generator that generates one or more trigger signals, and an input unit that receives an operation by an operator, wherein the biometric method comprises:
determining, by the calculation device, one or more specific intervals of the first time series data in response to the one or more trigger signals output from the trigger signal generator;
configuring, by the calculation device, a classification reference for classifying the time series data in the one or more specific intervals using the time series data in a first specific interval of the one or more specific intervals, while using an input signal from the input unit as a trigger;
classifying, by the calculation device using a result of classifying the first time series data based on the configured classification reference, the second time series data in the one or more specific intervals; and
causing, by the calculation device, the display device to display a result of classifying the second time series data.

18. The non-transitory computer readable recording medium according to claim 17, wherein the time series data is waveform data, and
wherein the biometric method further comprises:
configuring, by the calculation device, a reference amplitude that is the classification reference based on a maximum amplitude of the waveform data in the first specific interval of the one or more specific intervals determined by the input signal as the trigger, in the waveform signal in the specific intervals obtained by the first measuring device by measurement; and
upon determining, by the calculation device, that the waveform data in a second specific interval of the one or more specific intervals obtained by the first measuring device by the measurement exceeds the reference amplitude, classifying, by the calculation device, the waveform data obtained by the second measuring device by measurement in the second specific interval of the one or more specific intervals as valid data.

19. The non-transitory computer readable recording medium according to claim 17, wherein the time series data is waveform data, and wherein the biometric method further comprises:

processing, by the calculation device, a plurality of time series data items of a respective plurality of systems from the first measuring device;

configuring, for each of the plurality of systems, by the calculation device, a reference amplitude that is the classification reference based on a maximum amplitude of the waveform data in the first specific interval of the one or more specific intervals determined by the input signal as the trigger, in the waveform signal in the one or more specific intervals obtained by the first measuring device by measurement; and upon determining, for each of the plurality of systems, by the calculation device, that the waveform data in a second specific interval of the one or more specific intervals obtained by the first measuring device by the measurement exceeds the reference amplitude, classifying, by the calculation device, the waveform data obtained by the second measuring device by measurement in the second specific interval of the one or more specific intervals as valid data.

* * * * *